United States Patent
Samadani et al.

(10) Patent No.: US 11,200,507 B2
(45) Date of Patent: Dec. 14, 2021

(54) SYSTEM AND METHOD FOR OPTIMAL SENSOR PLACEMENT

(71) Applicant: KONINKLIJKE PHILIPS N.V., Eindhoven (NL)

(72) Inventors: Ali Akbar Ahmad Samadani, Somerville, MA (US); Saman Parvaneh, Malden, MA (US)

(73) Assignee: Koninklijke Philips N.V., Eindhoven (NL)

( * ) Notice: Subject to any disclaimer, the term of this patent is extended or adjusted under 35 U.S.C. 154(b) by 503 days.

(21) Appl. No.: 16/263,421

(22) Filed: Jan. 31, 2019

(65) Prior Publication Data

US 2019/0244125 A1 Aug. 8, 2019

Related U.S. Application Data

(60) Provisional application No. 62/750,375, filed on Oct. 25, 2018, provisional application No. 62/625,932, filed on Feb. 2, 2018.

(51) Int. Cl.
| | |
|---|---|
| *G06F 7/60* | (2006.01) |
| *G06N 7/00* | (2006.01) |
| *H04L 29/08* | (2006.01) |
| *G06F 17/18* | (2006.01) |

(52) U.S. Cl.
CPC ............ *G06N 7/005* (2013.01); *G06F 17/18* (2013.01); *H04L 67/12* (2013.01)

(58) Field of Classification Search
CPC .................................................. G06N 7/005
USPC ............................................................ 703/2
See application file for complete search history.

(56) References Cited

U.S. PATENT DOCUMENTS

| | | | |
|---|---|---|---|
| 9,551,594 B1* | 1/2017 | Stamatakis | G06F 3/0482 |
| 10,182,746 B1* | 1/2019 | Demiralp | A61B 5/1123 |
| 2009/0315733 A1* | 12/2009 | Bischoff | G08B 21/0469 340/659 |

(Continued)

OTHER PUBLICATIONS

"A Profile of Older Americans: 2014"; Administration on Aging Administration for Community Living, U.S. Department of Health and Human Services, 2014, 17 Page Document.

(Continued)

*Primary Examiner* — Timothy A Mudrick

(57) ABSTRACT

A controller includes a memory that stores instructions and a processor that executes the instructions. The instructions cause the controller to execute a process that includes receiving sensor data from a first sensor and a second sensor. The sensor data includes a time-series observation representing a first activity and a second activity. The controller generates models for each activity involving progressions through states indicated by the sensor data from each sensor. The controller receives from each sensor additional sensor data including a time-series observation representing the first activity and the second activity. The controller determines likelihoods that the models generated a portion of the additional sensor data and calculates a pair-wise distance between each sensor-specific determined likelihood to obtain calculated distances. The calculated distances for each sensor are grouped, and a relevance of each sensor to each activity is determined by executing a regression model using the grouped calculated distances.

19 Claims, 12 Drawing Sheets

(56) References Cited

U.S. PATENT DOCUMENTS

| 2011/0066383 A1* | 3/2011 | Jangle | G06K 9/00342 |
| | | | 702/19 |
| 2011/0068931 A1* | 3/2011 | Abernethy | G08B 21/0423 |
| | | | 340/573.1 |
| 2017/0193177 A1* | 7/2017 | Kusens | G06K 9/00771 |

OTHER PUBLICATIONS

Bayer et al: "Fixing to Stay: A National Survey of Housing and Home Modification Issues"; AARP Research Group, May 2000, 82 Page Document.

Statistics Canada: "The Canadian Population In 2011: Population Counts and Growth" Retrieved From http://www12.statcan.gc.ca/census-recensement/2011/as-sa/98-310-x2011001-eng.cfm, 13 Page Document.

Haux et al: "Health-Enabling and Ambient Assistive Technologies: Past, Present, Future"; IMIA Yearbook of Medical Informatics, 2016, pp. S76-S91.

Meier et al: "The Group Lasso for Logistic Regression"; J.R. Statis. Soc. B (2008), 70, PART 1, pp. 53-71.

Federal Interagency Forum on Aging Related Statistics: "Older Americans 2012:Key Indicators of Well-Being"; 200 Page Document.

Rabiner et al: "An Introduction to Hidden Markov Models"; IEEE ASSP Magazine, Jan. 1986, pp. 4-16.

Koch et al: "On Health-Enabling and Ambient-Assistive Technologies: What Has Been Achieved and Where Do We Have to Go"; Methods Inf Med Jan. 2009, pp. 29-37.

\* cited by examiner

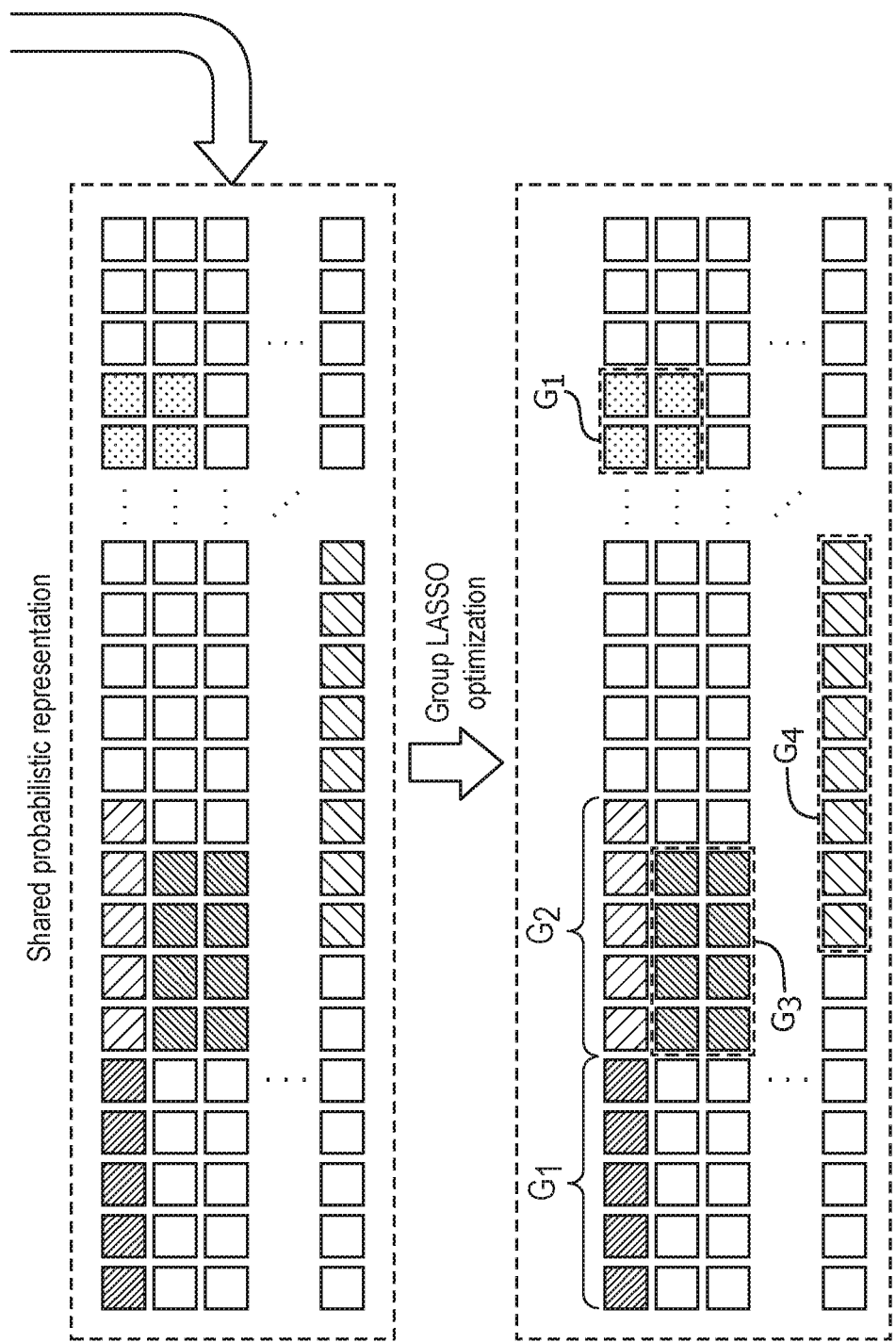

SYSTEM AND METHOD FOR OPTIMAL SENSOR PLACEMENT

CROSS REFERENCE TO RELATED APPLICATIONS

This application claims the benefit of U.S. Provisional Patent Application No. 62/750,375 filed on Oct. 25, 2018 and U.S. Provisional Application No. 62/625,932 filed on Feb. 2, 2018. These applications are hereby incorporated by reference herein.

BACKGROUND

Sensing technologies may require arrangements of sensors for ambient sensing and/or physiological sensing. The number and placement of sensors in the arrangements may vary based on context. For example, ambient sensing of activity of daily living (ADL) for various individuals, including, but not limited to, at-risk individuals is an emerging field of technology. ADLs include getting around a home to prepare a meal, eat, and use the toilet. By way of example, at-risk individuals may include individuals with cognitive impairment and/or physical disability.

In ambient sensing scenarios, the number, location, and type of sensors in an arrangement are commonly selected in an ad-hoc manner. This results in inefficiencies such as unnecessary costs and irrelevant data streams. This ad hoc placement also presents many technical challenges related to, for example, the data that is captured and/or the processing or determinations associated with the captured data. For example, ad hoc placement may result in obscuring data streams most salient to the activities/events of interests, impeding predictive and discriminative analysis of the ADLs and/or increasing computational and maintenance expenses.

Demographics are contributing to the increased use of ambient sensing technologies. For instance, the U.S. population 65 or older grew by 28% from 2004 to 2014 to approximately 46.2 million people and is projected to grow to 82.3 million by the year of 2040. The U.S. population 85 or older is projected to triple from approximately 6.2 million in 2014 to approximately 14.6 million in 2040. In the United States, 93% of Medicare beneficiaries 65 and older are aging in place, so as to stay in their own homes and communities as they age. In Canada, 92% of individuals 65 and older are aging in place. According to the American Association of Retired Persons (AARP), 90% of seniors 65 and older prefer to age in place. The demographic shift to an older population means that the younger caregiving segment of the population is shrinking. This and the burgeoning older population necessitates development of technologies that enable independent and healthy aging in place.

Determining an arrangement of sensor to be deployed in an ambient setting such as a user's home is often a challenging task, especially due to difference in a) floor map of users' home, b) users' physical build and lifestyle, and c) experience level of a technician that sets up the sensors. Additionally, as sensing technologies advance, sensor outputs are often multi-modal and multi-variate time-series observations, some of which are unnecessary and contribute to the inefficient irrelevant and or redundant data streams noted above. The irrelevant and/or redundant modalities and variables confound discriminative analysis and obscure the true mapping between the observed data streams and corresponding activities. For instance, in an ambient health monitoring setup, it is often unclear what types, numbers and locations of sensors will enable seamless observation of ADLs.

Conventional approaches do not account for temporal dependencies between sequentially-observed sensor data and may require a fixed-length representation of the sequential observations. For example, time-series signals are often represented in terms of a set of predefined discrete single-valued meta-features such as maximum, minimum, or variance of signals. However, streams of sensor data collected in a naturalistic setting often reflect temporal dependencies and are not inherently constrained to fixed-length representation. That is, in a naturalistic setting, activities may vary in terms of time, phase, action sequence order, and behavior, and may result in variations in sensor data associated with the same activity, thus, rendering the activity recognition difficult.

Selection of proper set of meta-features is critical for subsequent exploratory and predictive analysis. However, these meta-features are often selected in an ad-hoc manner without regard to saliency of temporal progression of an action sequence. Furthermore, time-series observations need to be spatiotemporally-aligned in order to obtain a homogeneous set of meta-features across different observations. More importantly, these meta-features do not capture the dynamic characteristics and temporal progression salient to the events of interest.

Therefore, an approach is needed to identify salient time-series variables that explicitly encodes temporal progression of sensor data and enable handling variable-length time-series observations. In ambient sensing, such an approach will help reduce numbers of sensors to only the salient ones, which in turn results in a more efficient, accurate, and inexpensive solution. Accordingly, systems and methods to determine an optimal number of placement of sensing technologies is needed.

SUMMARY

According to an aspect of the present disclosure, a controller for determining an arrangement of sensors includes a memory that stores instructions and a processor that executes the instructions. When executed by the processor, the instructions cause the controller to execute a process that includes receiving, from a first sensor of at least two sensors, a first sensor data including at least one time-series observation representing at least a first activity and a second activity; and receiving, from a second sensor of the at least two sensors, a second sensor data including at least one time-series observation representing the first activity and the second activity. The process also includes generating, by the processor, a first model for the first activity involving a first progression through multiple states indicated by at least a portion of the first sensor data; generating, by the processor, a second model for the second activity involving a second progression through multiple states indicated by at least a portion of the first sensor data; generating, by the processor, a third model for the first activity involving a third progression through multiple states indicated by at least a portion of the second sensor data; and generating, by the processor, a fourth model for the second activity involving a fourth progression through multiple states indicated by at least a portion of the second sensor data. The process further includes receiving, from the first sensor, a third sensor data including at least one time-series observation representing at least the first activity and the second activity; and receiving, from the second sensor, a fourth sensor data including at least one time-series observation representing at least the first activity and the second activity. The process moreover includes determining, using the processor, a likelihood that the first model generated at least a portion of the third sensor data, a likelihood that the second model generated at least a portion of the third sensor data, a likelihood that the third model generated at least a portion of the fourth sensor data, and a likelihood that the fourth model generated at least a portion of the fourth sensor data. The processor also calculates a pair-wise distance between each sensor-specific determined likelihood to obtain calculated distances, groups the calculated distances for the likelihoods involving the first sensor, and groups the calculated distances for the likelihoods involving the second sensor, to obtain grouped calculated distances. Finally, the process includes determining a first relevance of the first sensor and a second relevance of the second sensor for capturing the first activity and the second activity by executing a regression model using the grouped calculated distances.

According to another aspect of the present disclosure, a method for determining an arrangement of sensors includes receiving, from a first sensor of at least two sensors, a first sensor data including at least one time-series observation representing at least a first activity and a second activity; and receiving, from a second sensor of the at least two sensors, a second sensor data including at least one time-series observation representing the first activity and the second activity. The method also includes generating a first model for the first activity involving a first progression through multiple states indicated by at least a portion of the first sensor data; generating a second model for the second activity involving a second progression through multiple states indicated by at least a portion of the first sensor data; generating a third model for the first activity involving a third progression through multiple states indicated by at least a portion of the second sensor data; and generating a fourth model for the second activity involving a fourth progression through multiple states indicated by at least a portion of the second sensor data. The method further includes receiving, from the first sensor, a third sensor data including at least one time-series observation representing at least the first activity and the second activity; and receiving, from the second sensor, a fourth sensor data including at least one time-series observation representing at least the first activity and the second activity. The method moreover includes determining a likelihood that the first model generated at least a portion of the third sensor data, a likelihood that the second model generated at least a portion of the third sensor data, a likelihood that the third model generated at least a portion of the fourth sensor data, and a likelihood that the fourth model generated at least a portion of the fourth sensor data. The method also includes calculating a pair-wise distance between each sensor-specific determined likelihood to obtain calculated distances, grouping the calculated distances for the likelihoods involving the first sensor, and grouping the calculated distances for the likelihoods involving the second sensor, to obtain grouped calculated distances. Finally, the method includes determining a first relevance of the first sensor and a second relevance of the second sensor for capturing the first activity and the second activity by executing a regression model using the grouped calculated distances.

According to yet another aspect of the present disclosure, a system for determining an arrangement of sensors includes a communications interface used to communicate over a communications network; a user interface; and a controller including a memory that stores instructions and a processor that executes the instructions. When executed by the processor, the instructions cause the system to execute a process that includes receiving, from a first sensor of at least two sensors, a first sensor data including at least one time-series observation representing at least a first activity and a second activity; and receiving, from a second sensor of the at least two sensors, a second sensor data including at least one time-series observation representing the first activity and the second activity. The process also includes generating, by the processor, a first model for the first activity involving a first progression through multiple states indicated by at least a portion of the first sensor data; generating, by the processor, a second model for the second activity involving a second progression through multiple states indicated by at least a portion of the first sensor data; generating, by the processor, a third model for the first activity involving a third progression through multiple states indicated by at least a portion of the second sensor data; and generating, by the processor, a fourth model for the second activity involving a fourth progression through multiple states indicated by at least a portion of the second sensor data. The process further includes receiving, from the first sensor, a third sensor data including at least one time-series observation representing at least the first activity and the second activity; and receiving, from the second sensor, a fourth sensor data including at least one time-series observation representing at least the first activity and the second activity. The process moreover includes determining, using the processor, a likelihood that the first model generated at least a portion of the third sensor data, a likelihood that the second model generated at least a portion of the third sensor data, a likelihood that the third model generated at least a portion of the fourth sensor data, and a likelihood that the fourth model generated at least a portion of the fourth sensor data. The processor also calculates a pair-wise distance between each sensor-specific determined likelihood to obtain calculated distances, groups the calculated distances for the likelihoods involving the first sensor, and groups the calculated distances for the likelihoods involving the second sensor, to obtain grouped calculated distances. Finally, the process includes determining a first relevance of the first sensor and a second relevance of the second sensor for capturing the first activity and the second activity by executing a regression model using the grouped calculated distances.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
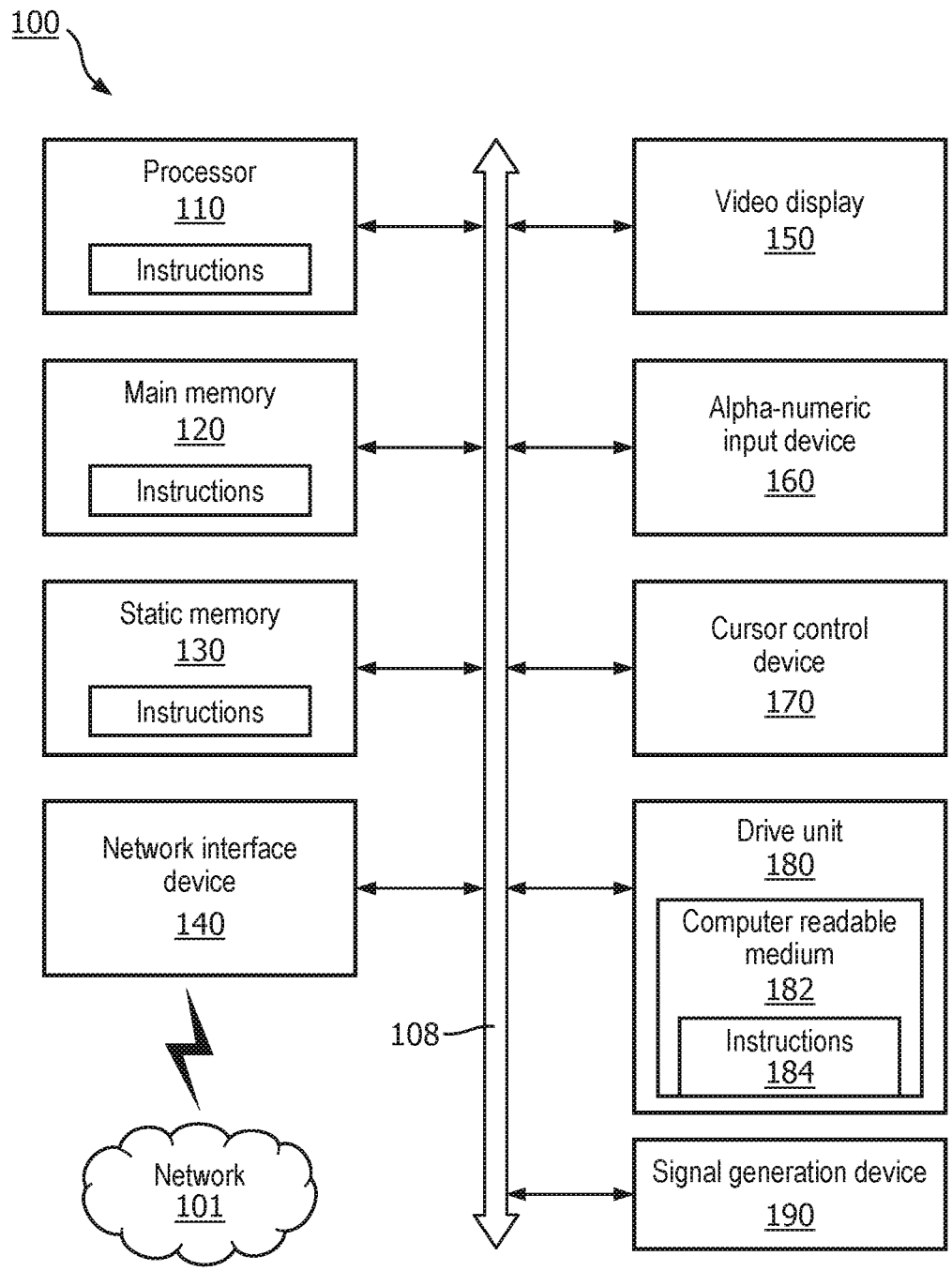
FIG. 1 illustrates a general computer system, on which a method of determining an arrangement of sensors can be implemented, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Various embodiments of the present disclosure provide systems, methods, and apparatus for determining an optimal configuration of sensor placement. Advantageously and in an exemplary embodiment, a system for determining an optimal sensor configuration may include determining an optimal ambient sensor confirmation, determining an optimal physiological sensor configuration, and/or determining an optimal configuration of a combination of ambient and/or physiological sensing technologies. Although described separately, the methods of determining ambient sensing technology configurations may be used in conjunction with the methods of determining physiological sensing technology configurations.

Regarding ambient sensing technologies, systems and methods described herein may automatically identify a minimal set of ambient sensors and their optimal employment to monitor and best track activities of daily living (ADL). The systems and methods described herein may incorporate a number of data points to determine optimal sensor configurations, such as raw sensor data obtained during a training period, floorplan or layout data associated with the sensing environment, a user's weight, height, and/or build information, a user's medical condition, an installment technician's skill level, and/or other data that may be relevant.

FIG. 1 illustrates a general computer system, on which a method of determining an arrangement of sensors can be implemented, in accordance with a representative embodiment.

FIG. 1 is an illustrative embodiment of a general computer system, on which a method of optimal sensor placement can be implemented. The computer system 100 can include a set of instructions that can be executed to cause the computer system 100 to perform any one or more of the methods or computer-based functions disclosed herein. The computer system 100 may operate as a standalone device or may be connected, for example, using a network 101, to other computer systems or peripheral devices.

In a networked deployment, the computer system 100 may operate in the capacity of a server or as a client user computer in a server-client user network environment, or as a peer computer system in a peer-to-peer (or distributed) network environment. The computer system 100 can also be implemented as or incorporated into various devices, such as a stationary computer, a mobile computer, a personal computer (PC), a laptop computer, a tablet computer, a wireless smart phone, a personal digital assistant (PDA), or any other machine capable of executing a set of instructions (sequential or otherwise) that specify actions to be taken by that machine. The computer system 100 can be incorporated as or in a device that in turn is in an integrated system that includes additional devices. In an embodiment, the computer system 100 can be implemented using electronic devices that provide voice, video or data communication. Further, while the computer system 100 is illustrated in the singular, the term "system" shall also be taken to include any collection of systems or sub-systems that individually or jointly execute a set, or multiple sets, of instructions to perform one or more computer functions.

As illustrated in FIG. 1, the computer system 100 includes a processor 110. A processor for a computer system 100 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 100 is configured to execute software instructions to perform functions as described in the various embodiments herein. A processor for a computer system 100 may be a general-purpose processor or may be part of an application specific integrated circuit (ASIC). A processor for a computer system 100 may also be a microprocessor, a microcomputer, a processor chip, a controller, a microcontroller, a digital signal processor (DSP), a state machine, or a programmable logic device. A processor for a computer system 100 may also be a logical circuit, including a programmable gate array (PGA) such as a field programmable gate array (FPGA), or another type of circuit that includes discrete gate and/or transistor logic. A processor for a computer system 100 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 100 may include a main memory 120 and/or a static memory 130, where the memories may communicate with each other via a bus 108. Memories described herein are tangible storage mediums that can store data and executable instructions and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 100 may further include a video display unit 150, such as a liquid crystal display (LCD), an organic light emitting diode (OLED), a flat panel display, a solid-state display, or a cathode ray tube (CRT). Additionally, the computer system 100 may include an input device 160, such as a keyboard/virtual keyboard or touch-sensitive input screen or speech input with speech recognition, and a cursor control device 170, such as a mouse or touch-sensitive input screen or pad. The computer system 100 can also include a disk drive unit 180, a signal generation device 190, such as a speaker or remote control, and a network interface device 140.

In an embodiment, as depicted in FIG. 1, the disk drive unit 180 may include a computer-readable medium 182 in which one or more sets of instructions 184, e.g. software, can be embedded. Sets of instructions 184 can be read from the computer-readable medium 182. Further, the instructions 184, when executed by a processor, can be used to perform one or more of the methods and processes as described herein. In an embodiment, the instructions 184 may reside completely, or at least partially, within the main memory 120, the static memory 130, and/or within the processor 110 during execution by the computer system 100.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 182 that includes instructions 184 or receives and executes instructions 184 responsive to a propagated signal; so that a device connected to a network 101 can communicate voice, video or data over the network 101. Further, the instructions 184 may be transmitted or received over the network 101 via the network interface device 140.

Figure 2A:
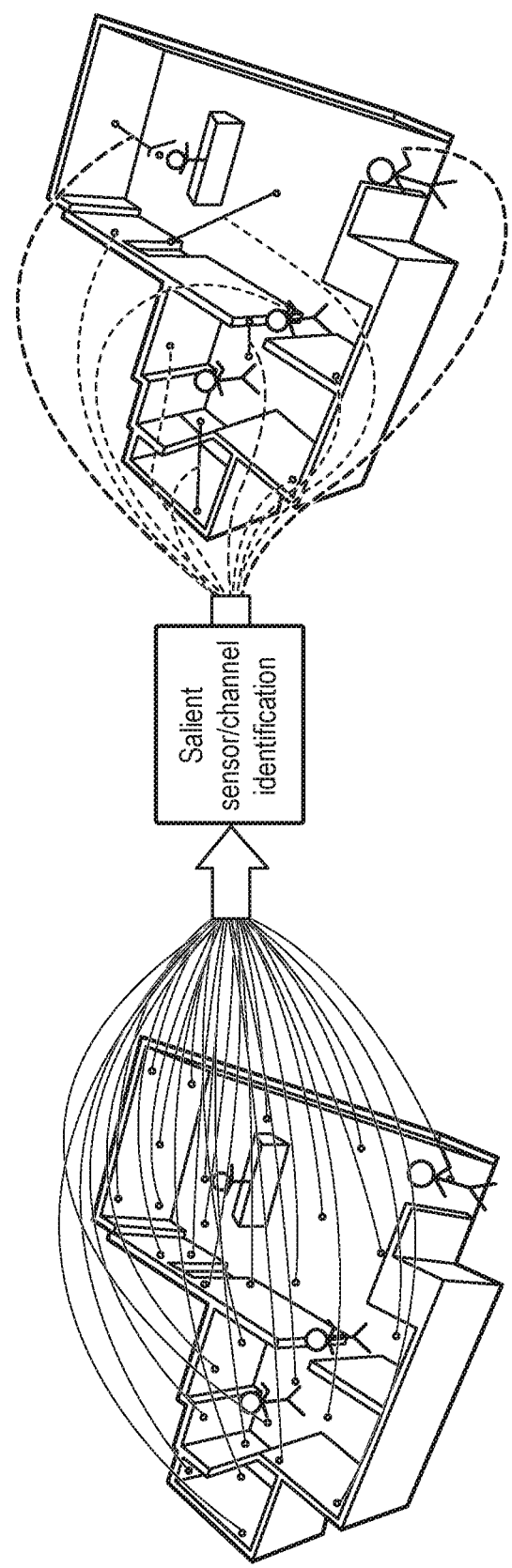
FIG. 2A is an illustrative view of a building layout for determining an arrangement of sensors, in accordance with a representative embodiment.

FIG. 2A is an illustrative view of a building layout for determining an arrangement of sensors, in accordance with a representative embodiment.

FIG. 2A illustrates a schematic presentation of an example embodiment. In FIG. 2A, an algorithmic framework augments a multi-sensor, multi-modal installation for home-monitoring. The algorithm receives activity-specific streams of raw-data captured by the sensors and constructs a high-level abstraction of the data streams. The resulting abstraction of sensor data is then used to determine individual sensors salient to accurately capturing ADLs and IADLs. Furthermore, the proposed algorithm identifies pairs of sensors whose correlation or sequence of activity is important to capture ADLs and IADLs. For instance, for monitoring a walking behavior from a bedroom to a bathroom, the correlation and the sequence of activity of a hallway sensor and the bathroom door sensor are salient for accurate detection of the toileting behavior. The hallway sensor and the bathroom door sensor may be placed in locations specifically intended to detect particular activities such as movement in the hallway or the bathroom door opening or closing. Other examples of activity that may be the subject of activity-specific streams include a person falling or the person walking.

The features disclosed herein may be used in the installation phase of a multi-sensor/multi-modal (ambient pressure and motion sensors, vision sensors) home-monitoring system to simulate different user scenarios and determine the minimal set of sensors and their placement for optimal monitoring of user's activities. Furthermore, user-specific factors (e.g., physical build) and specifics of floor plan can be incorporated in the modelling to identify a more user-aware set of sensors. As such, the features disclosed herein enable tailoring the home-monitoring solution for each user separately, and in return, help promoting an accurate and user-aware home-monitoring solution. The proposed salient sensor/channel identification is described in detail in the next section. For example, as shown in the illustration on the left in FIG. 2A, initial sensors may be placed in various positions around a layout.

Raw sensor data may be obtained and used to determine a minimal number of sensors and required sensor placement to recognize a particular event or activity of interest. On the right side of FIG. 2A, the schematic illustrates identified salient sensors and channel pairs (illustrated via a dashed line, whereby the thickness of the dashed line corresponds to the relative weight or importance of the sensor) for detecting an activity of interest. By way of example, as illustrated in FIG. 2A, for monitoring a walking behavior from a bedroom to a bathroom, the correlation and sequence of activity of a hallway sensor and a bathroom door sensor may be salient for accurate detection of washroom behavior. Ambient sensors may include sensors placed around a location, but activities of daily living may also be monitored using wearable sensors. Examples of ambient sensors that can be used include, but are not limited to:

motion sensors such as infrared sensors or SONAR sensors
temperature sensors
humidity sensors
light sensors
electricity sensors
pressure sensors
camera sensors such as security cameras Motion sensors may be, for example, binary infrared sensors that detect either the presence or non-presence of an obstruction in a path of infrared light. For example, an infrared motion sensor may detect an object in front of the infrared motion sensor. Motion sensors may, for example, detect motion of a door opening or closing. Humidity sensors may be used, for example, to detect incontinence, or someone taking a bath or shower. An electricity sensor may for example, detect appliance usage, such as how long a television is on, how long a light is on, and/or other characteristics of an electrical device. Pressure sensors may, for example, detect a pose of a person sleeping when placed in or under a mattress and may be used to alert nursing staff to adjust a pose.

The various sensors described in FIG. 2A may include multi-sensor, multi-modal sensors such as ambient pressure sensors, motion sensors, vision sensors, and/or the like. For example, reference to a first sensor herein may be to a first group of sensors, and reference to a second sensor herein may be to a second group of sensors. Each sensor of a first group of sensors and a second group of sensors may sense the same type (mode) of characteristics. Additionally, different sensors within a first group of sensors and a second group of sensors may sense different types (modes) of characteristics.

In the embodiment of FIG. 2A, the arrangement of sensors may include number and location of sensors. Location may be identified by characteristics such as other (non-sensor) elements near a sensor such as doors, windows and drawers. Location may be identified by a particular type of room or other space in a building such as kitchen, bathroom, hall, basement and so on. Beyond the raw data streams that are used in the determinations of an optimal sensor configuration as described herein, other variables such as location may be used either in a measurement form or a binary form. Measurement forms include, but are not limited to, e.g., height measurement, weight measurement, BMI measurement, distance between floor and ceiling, room area, length/wide measurements of a room, humidity measurements, temperature measurements, and/or the like. Binary forms may include, for example, presence of a pet (Y/N), height above/below a threshold (Y/N), seasonal presence such as whether the current season is summer (Y/N), and/or the like.

In the embodiment of FIG. 2A, optimal sensor/channel set placement can be identified for a living arrangement to sense ADLs for a user. The dashed lines on the left indicate the stream of raw sensor data which are fed into controller described herein, to be subject to an algorithm to identify the optimal sensor arrangement. On the right side of FIG. 2A the identified salient sensors and channel pairs are shown as dashed lines. The thickness of the dashed lines on the right side indicate the importance of the corresponding sensor for detecting the activity of interest. A solid line between sensors on the right indicates an identified salient pair-wise correlation for recognizing an activity of interest.

An example context for the embodiment of FIG. 2A is sensors placed around a home. Another example context for the embodiment of FIG. 2A is sensors placed around a nursing home.

Figure 2B:
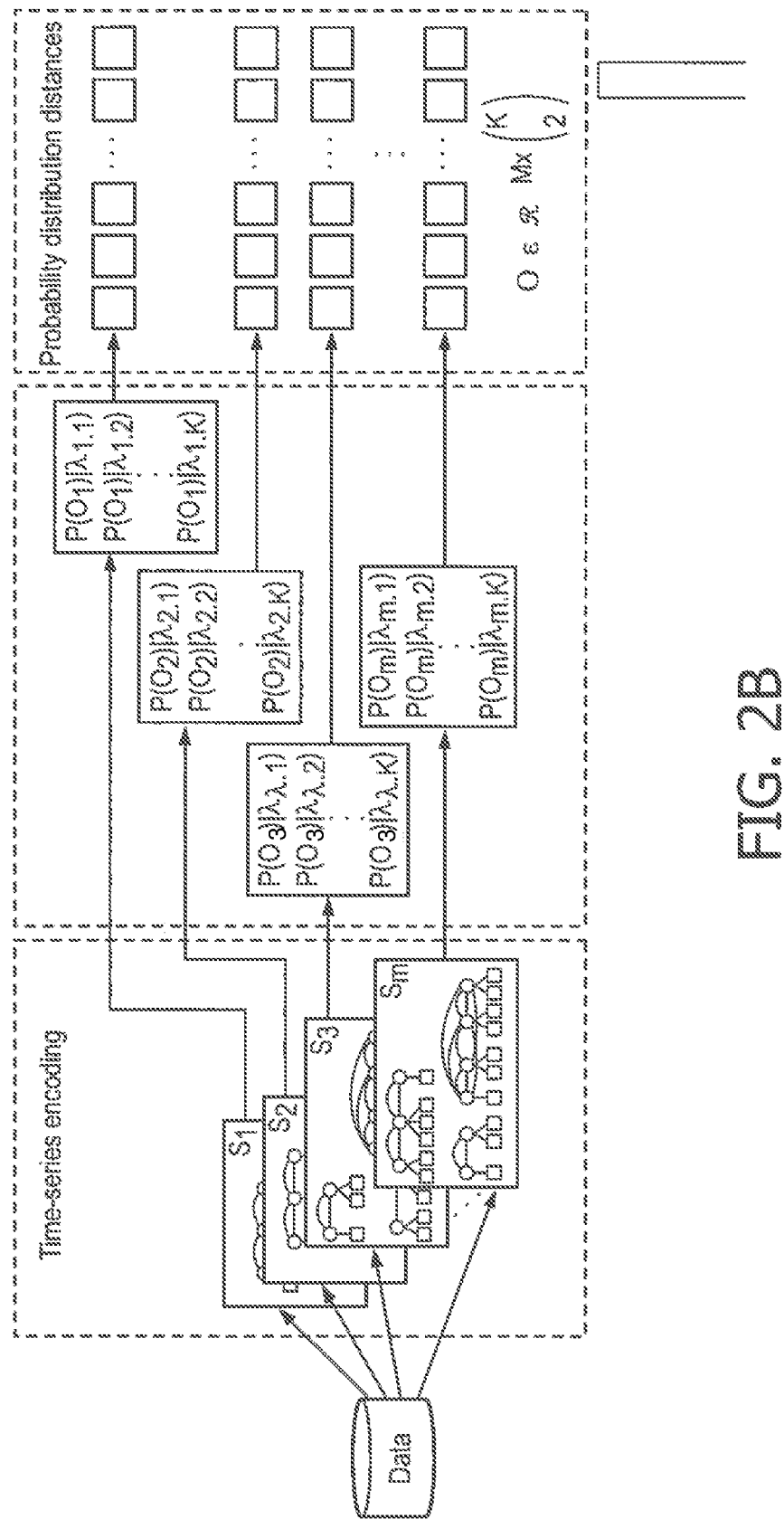
FIG. 2B is an illustrative view of a model for determining an arrangement of sensors, in accordance with a representative embodiment.

FIG. 2B is an illustrative view of a model for determining an arrangement of sensors, in accordance with a representative embodiment.

FIG. 2B illustrates an example model for salient sensor and/or channel identification that obtains a hybrid generative-discriminative abstraction of multi-variate time-series observations (sensor data streams). A model or models as described herein may refer to a probabilistic graphical model. For example, as illustrated in FIG. 2B, the raw data received via the placed sensors may be encoded as activity-specific time-series observations in a stochastic model or a dynamic Bayesian network (e.g., separate hidden Markov models (HMM)).

In this manner, temporal information of sensor data streams may be embedded as a dynamic stochastic process. Next, the sensor data streams may be projected in the posterior space of the resulting activity-specific models (e.g., HMMs), hence repurposing the models (e.g., HMMs)

for a systematic time-series representation. Progressions through each state of an activity sensed by each sensor may be accumulated and analyzed to determine the probability of any one state resulting next in the same or another state. Then, distances between activity-specific probability distributions may be computed. These resulting probability distances may be aggregated to obtain a shared probabilistic representation of the sensor data. Dimensions of the resulting shared probabilistic space may be automatically weighted according to their relevance to distinguishing between different events and activities using the Group LASSO regression. The Group LASSO regression may apply a multinomial logistic regression model with a group LASSO penalty or a binomial logistic regression model with a group LASSO penalty. Additional sensor data may be received from the sensors following the original modeling, and then applied to determine the likelihood that any particular model generated the additional sensor data. The determined likelihoods are associated with the first sensor and with the second sensor. And, minimal set of sensors may be identified as most salient for tracking and detecting events and activities of interests based on the weights determined. The minimal set of sensors may be minimized group of sensors from the initial sensors, such as a subset of the initial sensors.

This approach illustrated in FIG. 2B may apply the group-LASSO penalty on the posterior probabilities (or affinity matrix constructed based on symmetric Kullback-Leibler divergence between posteriors) estimated by the forward algorithm and hidden Markov models of the multivariate time-series observations. In this manner, a multinomial logistic regression model with group LASSO penalty is applied over posteriors of the generative networks with each group corresponding to posteriors of a sensor. Accordingly, the system may provide a systematic framework to optimize the number of sensors and their placement needed to capture a target event, activity and/or phenomenon. And, this methodology overcomes one of the limitations of conventional feature selection techniques where observations need to be of a fixed length, which is problematic with raw sensor data where in a naturalistic setting, the data is not typically of a fixed length.

With respect to ambient sensor placement for ADLs, there may be an abundance of multi-modal, multi-variate time-series observations, not all of which are relevant to discriminating between activities of interest, related to the sensors used for sensing the ADL activities. The presence of irrelevant time-series data poses several challenges, such as obscuring data streams most salient to activities of interest, impeding predictive and discriminative analysis, and adding computational, storage, and maintenance expenses. The systems and methods described herein, however, identify time-series modalities and channels salient to discriminating between activities of interest.

As described above for FIG. 2B, stochastic generative-discriminative encoding of sensor data can be regularized. Event-specific data streams may be encoded in a separate generative dynamic Bayesian network (e.g., hidden Markov model). Multinomial logistic regression with group LASSO penalty may be performed over posteriors of the generative networks with each group corresponding to posteriors of a sensor. Details specific to users living in the living space (e.g., user needs and physical build) can be incorporated in the regression to identify a more user-specific sensor deployment. The approach accounts for the time-series and variable-length nature of event-specific sensor data streams and can be applied to any number of dependent or independent sensors in multi-modal sensing settings. Identifying a minimal set of sensors most salient for detecting ADLs as in FIG. 2B helps promote efficient, low-cost, accurate ADL tracking and monitoring technologies. The resulting minimal set of sensors may be used to optimize sensor deployment for tracking activities of daily living in an ambient sensing setup such as for home monitoring.

Another explanation of the flow in FIG. 2B for the salient sensor/channel identification approach is that color-coded groups may correspond to sensor-specific variables. Of the sensor-specific variables, those relevant to the events of interest can be identified and returned as reflective of the minimal set of sensors that should be used. The m initial sensors are indicated as S1 to Sm. $\lambda_{m,k}$ indicates the HMM model encoding the kth activity captured through mth sensor. In FIG. 2B, $P(Om|\lambda_{m,k})$ is the posterior of the stream data from $m^{th}$ sensor (Om) being generated by $\lambda_{m,k}$, where posterior is synonymous here to conditional likelihood or probability. $G_n$ is a set of HMI parameters corresponding to the nth sensor.

Ultimately, the output of the flow in FIG. 2B can be used to identify relevance of sensors to activities monitored by the sensors. When the sensors sense progression of states reflective of activities sensed by the sensors, the flow helps identify the relevance of each sensor to each activity. Thus, when an initial group of sensors includes a first sensor and a second sensor that monitor a first activity and a second activity, the flow in FIG. 2B can be to determine which sensors are included and which sensors are excluded from a resultant arrangement used to monitor the space. Thus, of an initial set that includes a first sensor and a second sensor, one of the first sensor and the second sensor may be included in an arrangement based on the relevance to the activities, and the other of the first sensor and the second sensor may be excluded in the arrangement of sensors based on the relevance to the activities.

Figure 2C:
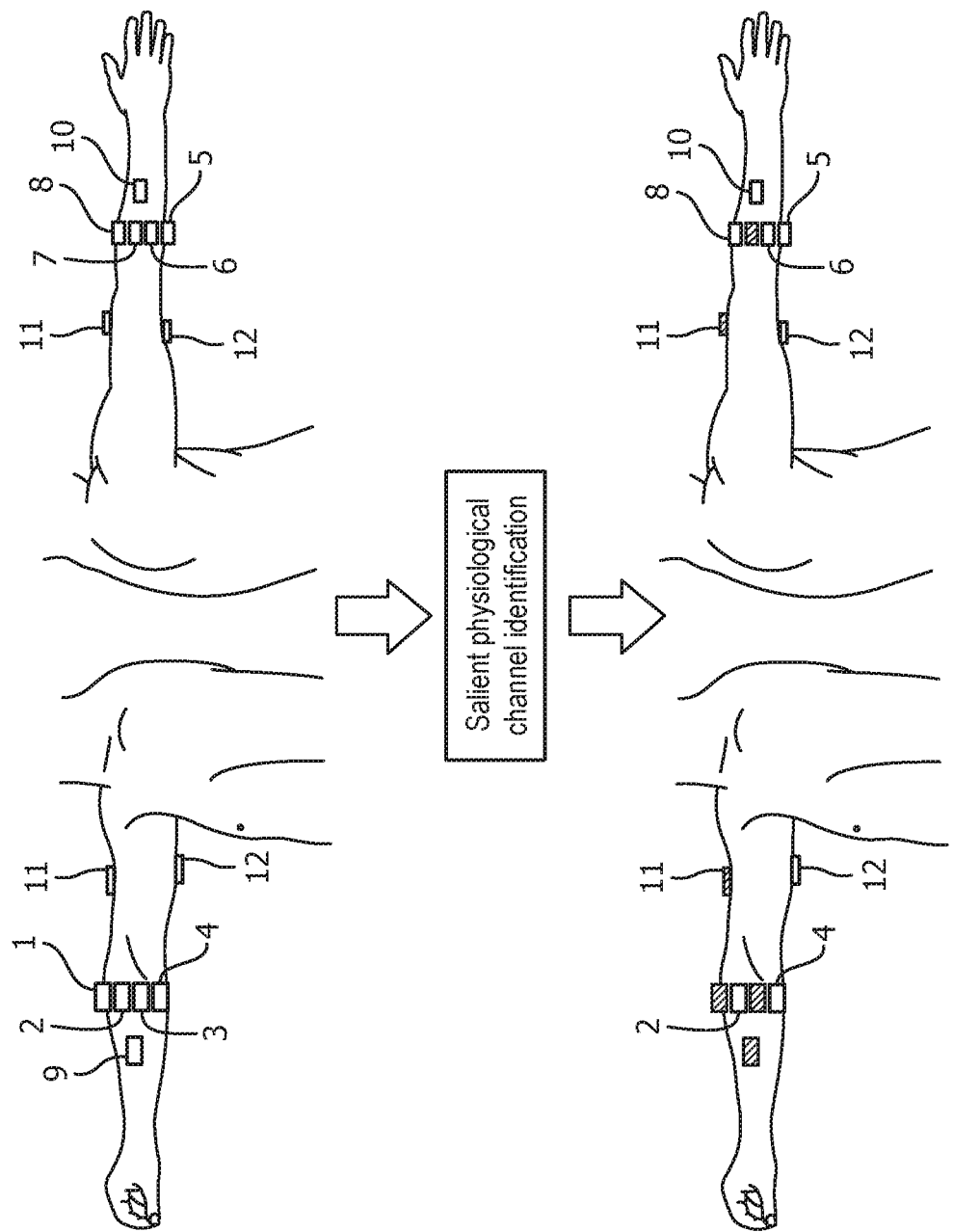
FIG. 2C is an illustrative view of a physiological layout for determining an arrangement of sensors, in accordance with a representative embodiment.

FIG. 2C is an illustrative view of a physiological layout for determining an arrangement of sensors, in accordance with a representative embodiment.

By way of example, FIG. 2C illustrates obtaining optimal sensor configurations for a physiological sensor used in hand gesture recognition. In this example, hand gestures may be detected from associated electromyographic (EMG) activities captured at arm and forearm. In this example, and in physiological sensor configuration generally, it may be important to identify how many sensors are required to detect specific events and/or activities, as well as where the sensors should be located to help discriminating between different events, such as hand gestures. The approach described herein may account for stochastic, interpersonal, timing, and phase variations.

Given multi-modal/multi-variate time-series observations, the system and methods described herein may identify a minimal set of time-series variables/modalities most salient to discriminating between different classes of the observations. For example, as illustrated in FIG. 2C, to reduce the number of sensors (1 to 12) illustrated in the top illustration to the sensors defined by the solid blocks (1, 3, 7, 9, and 11) in the bottom illustration, the following procedure may be used.

First, multi-variate time-series observations may be encoded into hybrid stochastic generative-discriminative models. Then, a shared probabilistic representation may be generated where observations are represented in terms of pair-wise distances between the stochastic models. Parameters of the resulting stochastic models may then be weighted using multinomial logistic regression with group LASSO penalty in the shared probabilistic space, with each group corresponding to sensor-specific distances (posterior distances between a sensor and the rest of the sensors for each activity). And finally, the system may determine salient sensor channels based on the weighted parameters, and classify observation based on the reduced sensor set.

The systems and methods that determine the optimal sensor configuration for physiological sensing technologies may be used to determine a general sensor configuration for a user of a particular height, weight, and/or build, or the systems and methods may be used to determine optimal sensor placement for a specific user based on specific user features (height, weight, BMI, physiological characteristics, user diagnosis and/or the like).

Systems and methods described herein may not only determine the number and placement of sensors but may also determine a sensor type (ECG, PPG, accelerometer, gyroscope, and/or the like).

Similar to the ambient sensing technologies optimal placement, the methods described herein for physiological sensing technology configurations may include the methods described above with respect to FIG. 2B. Using the methodology of FIG. 2B for physiological sensing technologies, various constraints specific to the ambient sensing technologies may be imposed. For example, constraints may be specified to ensure members of a set of sensors are always selected together (e.g., the involvement of both the flexor pollicis longus muscle and the flexor digitorum superficialis muscle to flex the thumb and bend fingers in making a first gesture). As such, the proposed approach will be constrained to (de)-select the interacting channels together based on their collective saliency to the classification task.

A priori information about sensor combinations may include details of a household arrangement, such as if a user lives with a pet. This kind of information that is particular to individual households can be used to arrange the initial set of sensors. For example, if the user lives with a pet, detection of the user's motion in the hallway may require motion sensors at heights of 1 foot and 5 feet to both activate simultaneously since activation of the sensor at 1 foot may be triggered solely by the pet. If the a priori information about sensor combinations is available, the approach illustrated in FIG. 2B can incorporate the a priori information to (de)select a combination of sensors (e.g., a sensor triplet) based on their collective saliency to detecting ADLs. Furthermore, the approach can incorporate information about user's physical build (e.g., height), to identify a more user-aware set of sensors and their deployment.

If information about sensor combinations and/or environment is available prior to final configuration, those data points may be included in the calculation process. By way of example, if a user lives with a pet, to detect user's motion in the hallway, two motion sensors may be needed, one at a low height (e.g., one foot off the ground) and a second at a higher height (e.g., five feet off the ground) whereby the sensors may be required to be activated simultaneously.

Where initial raw sensor data is unavailable, image layouts, user data, and/or other known data may be used to model sensor placement, whereby the raw sensor data may be simulated using the image layouts, user data, and/or other known data sources.

Figure 3A:
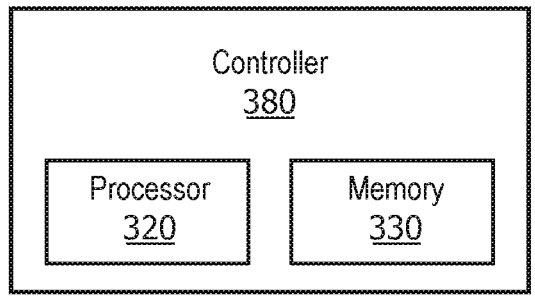
FIG. 3A is an illustrative view of a controller for determining an arrangement of sensors, in accordance with a representative embodiment.

FIG. 3A is an illustrative view of a controller for determining an arrangement of sensors, in accordance with a representative embodiment.

In FIG. 3A, a controller 380 includes a memory 330 that stores instructions and a processor 320 that executes the instructions. The controller 380 may be provided in a variety of devices, system and arrangements, including a mobile computer or tablet. The processor 320 may execute the instructions to implement part or all of methods described herein. Additionally, the controller 380 may be distributed among several devices, such as when methods are necessarily implemented in a distributed manner that requires multiples sets of memory/processor combinations.

Figure 3B:
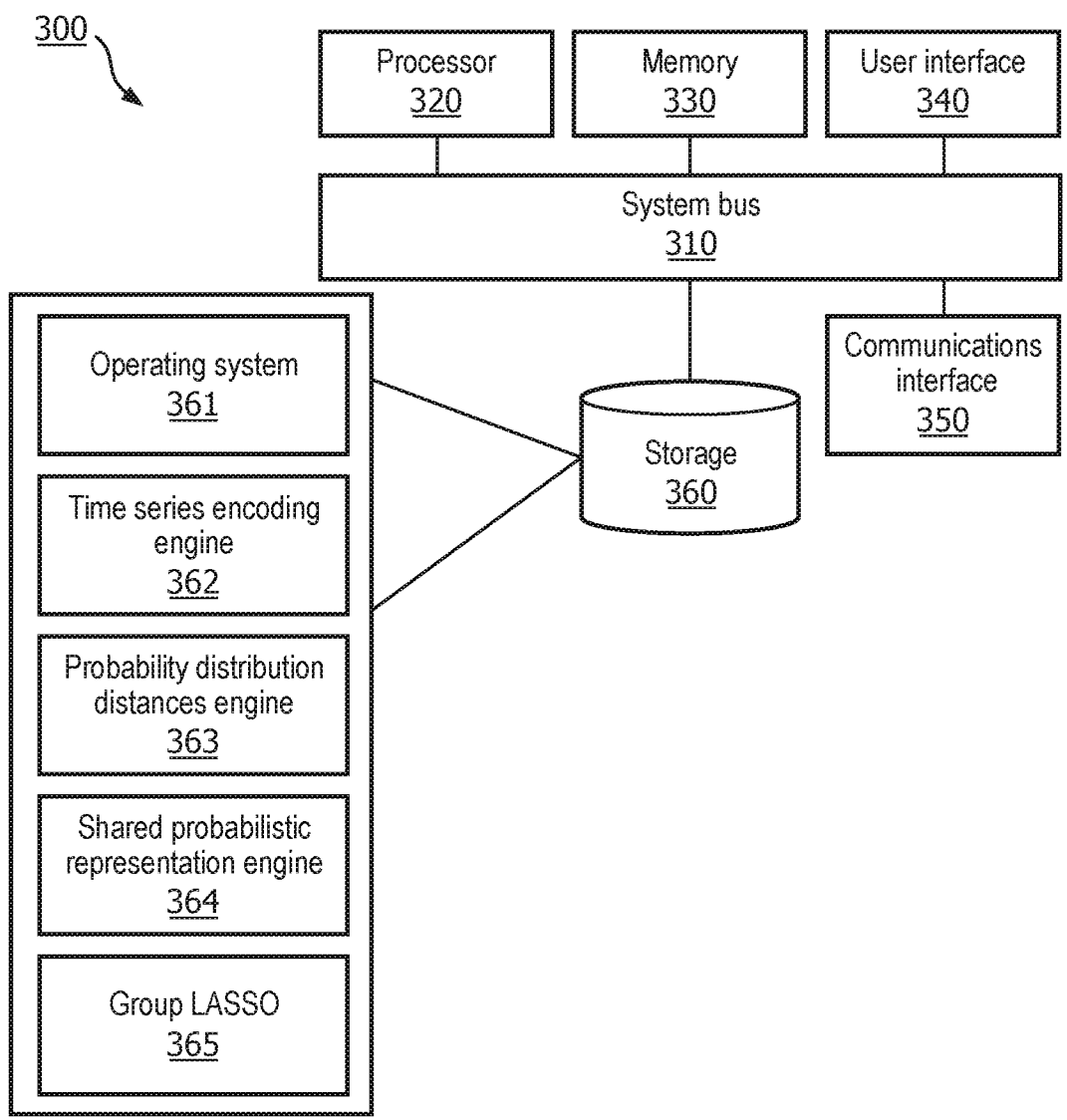
FIG. 3B is an illustrative view of a system for determining an arrangement of sensors, in accordance with a representative embodiment.

FIG. 3B is an illustrative view of a system for determining an arrangement of sensors, in accordance with a representative embodiment.

The system that executes the methods and/or models described herein may include, for example, a system 300 of hardware components as illustrated in FIG. 3B. For example, the system 300 may be a device such as a host device. As shown, the system 300 may include a processor 320, memory 330, user interface 340, communication interface 350, and storage 360 interconnected via one or more system buses 310. It will be understood that FIG. 3B constitutes, in some respects, an abstraction and that the actual organization of the components of the system 300 may be more complex than illustrated.

The processor 320 may be any hardware device capable of executing instructions stored in memory 330 or storage 360 or otherwise processing data. As such, the processor may include a microprocessor, field programmable gate array (FPGA), application-specific integrated circuit (ASIC), or other similar devices.

The memory 330 may include various memories such as, for example L1, L2, or L3 cache or system memory. As such, the memory 330 may include static random-access memory (SRAM), dynamic RAM (DRAM), flash memory, read only memory (ROM), or other similar memory devices. It will be apparent that, in embodiments where the processor includes one or more ASICs (or other processing devices) that implement one or more of the functions described herein in hardware, the software described as corresponding to such functionality in other embodiments may be omitted.

The user interface 340 may include one or more devices for enabling communication with a user such as an administrator, a clinician, a technician, a user, and/or a doctor. For example, the user interface 340 may include a display, a mouse, and a keyboard for receiving user commands. In some embodiments, the user interface 340 may include a command line interface or graphical user interface that may be presented to a remote terminal via the communication interface 350.

The communication interface 350 may include one or more devices for enabling communication with other hardware devices. For example, the communication interface 350 may include a network interface card (NIC) configured to communicate according to the Ethernet protocol. Additionally, the communication interface 350 may implement a TCP/IP stack for communication according to the TCP/IP protocols. Various alternative or additional hardware or configurations for the communication interface 350 will be apparent.

The storage 360 may include one or more machine-readable storage media such as read-only memory (ROM), random-access memory (RAM), magnetic disk storage media, optical storage media, flash-memory devices, or similar storage media. In various embodiments, the storage 360 may store instructions for execution by the processor 320 or data upon with the processor 320 may operate. For example, the storage 360 may store data associated with ambient sensing technologies, physiological sensing technologies (e.g., raw sensor data), data associated with any stage of the methodologies described herein including, for example, data from time-series encoding, probability distribution distance calculation, shared probabilities representations, and group LASSO optimizations. Where the system 300 implements the procedures as described herein, the storage 360 may include an operating system 361, a time series encoding engine 362, a probability distribution distances engine 363, a shared probabilistic representation engine 364, and a group LASSO 365. The time series encoding engine 362 may store executable instructions for encoding activity-specific time-series observations. The probability distribution distances engine 363 may store executable instructions for projecting sensor data streams in posterior space of resulting activity/event-specific models and computing distances between activity-specific probability distributions. The shared probabilistic representation engine 364 may store executable instructions for aggregating resulting probability distances to obtain shared probabilistic representations of sensor data. The group LASSO 365 may store executable instructions for weighting dimensions of resulting shared probabilistic spaces according to their relevance to distinguish between different events and activities, and for identifying a minimal set of sensors as most salient for tracking and detecting events or activities of interest. The storage 360 may store additional software components required to execute the functionality described herein, which also may control operations of the system 300.

It will be apparent that various information described as stored in the storage 360 may be additionally or alternatively stored in the memory 330. In this respect, the memory 330 may also be considered to constitute a "storage device" and the storage 360 may be considered a "memory." Various other arrangements will be apparent. Further, the memory 330 and storage 360 may both be considered to be "non-transitory machine-readable media." As used herein, the term "non-transitory" will be understood to exclude transitory signals but to include all forms of storage, including both volatile and non-volatile memories.

While the system 300 is shown as including one of each described component, the various components may be duplicated in various embodiments. For example, the processor 320 may include multiple microprocessors that are configured to independently execute the methods described herein or are configured to perform steps or subroutines of the methods described herein such that the multiple processors cooperate to achieve the functionality described herein. Further, where the system 300 is implemented in a cloud computing system, the various hardware components may belong to separate physical systems. For example, the processor 320 may include a first processor in a first server and a second processor in a second server.

Figure 4:
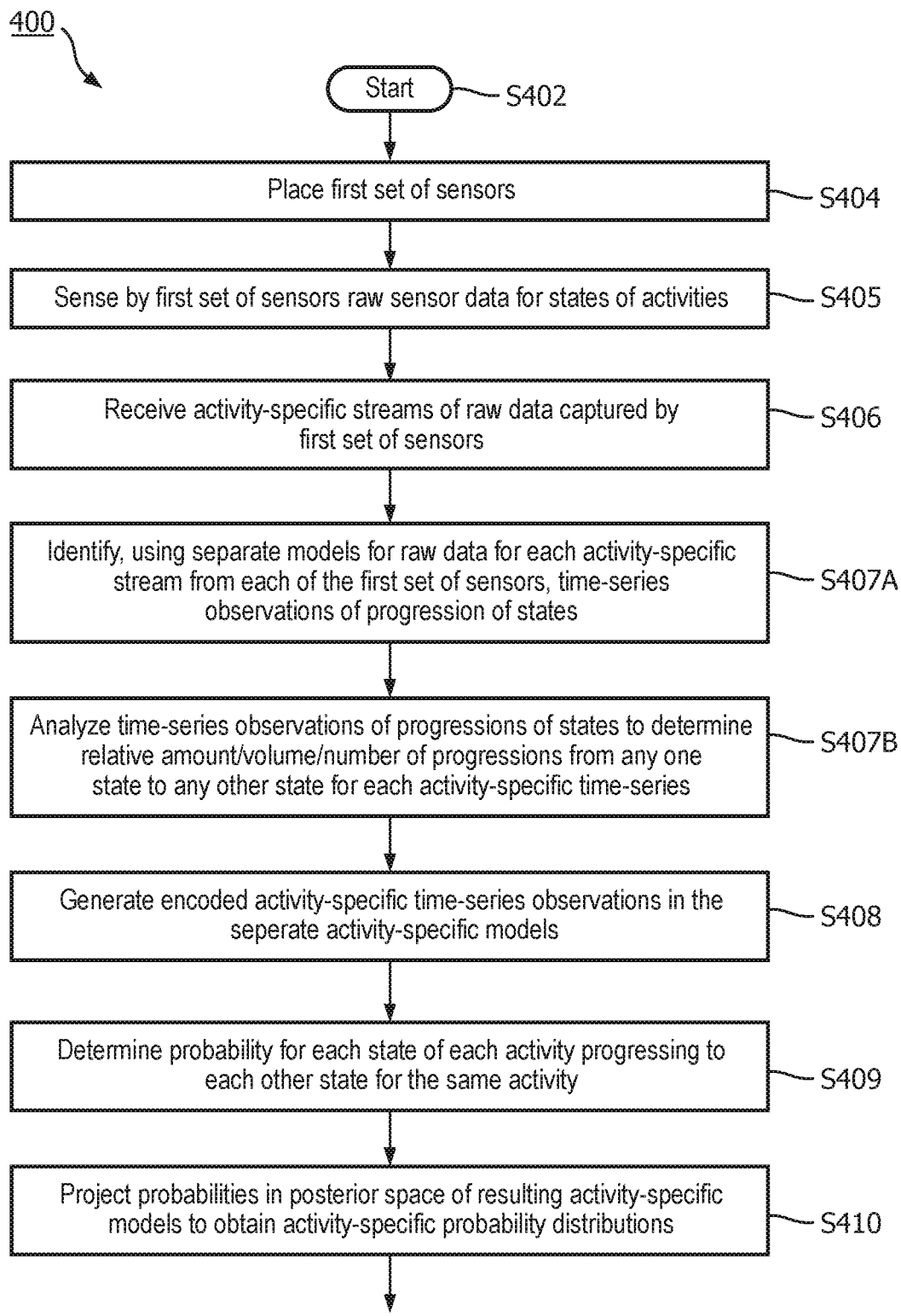
FIG. 4 illustrates a process for determining an arrangement of sensors, in accordance with a representative embodiment.
Figure 4:
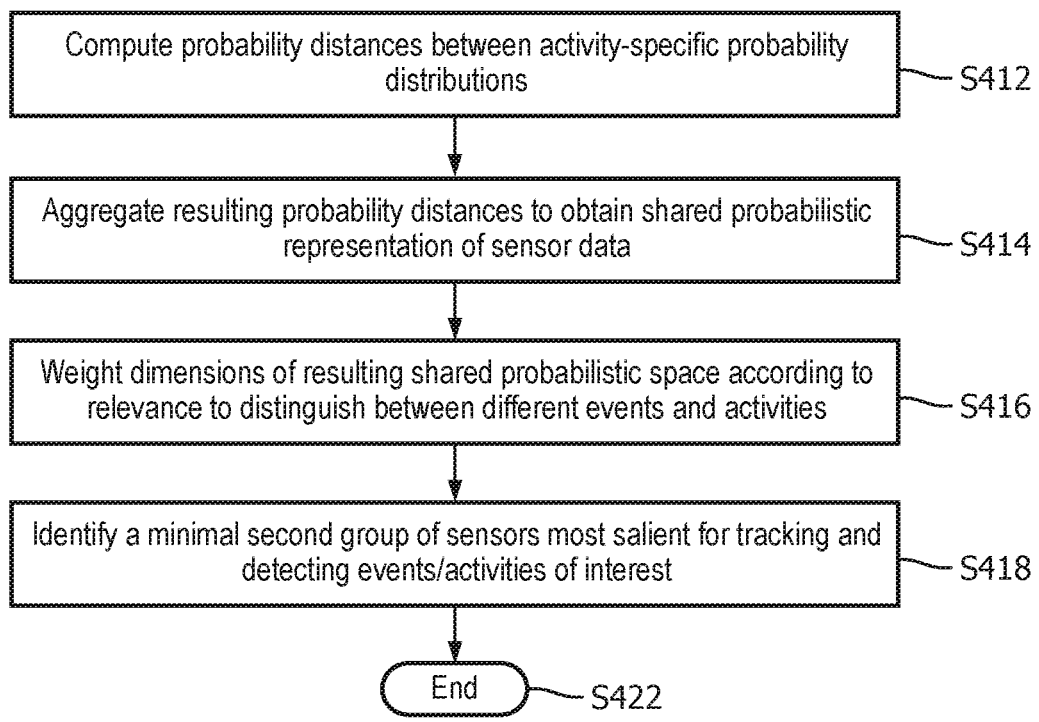

FIG. 4 illustrates a process for determining an arrangement of sensors, in accordance with a representative embodiment.

FIG. 4 illustrates a method 400 that may be executed by the various systems described herein. Method 400 may start at block S402. At block S404 initial sensors may be placed (such as the sensor placement in FIG. 2A and/or FIG. 2C). The sensors placed at S404 may be considered a first set of sensors. Method 400 may not require initial sensor placement but may require initial data input such as a floorplan and/or room configuration data (e.g., ceiling height, distance between objects, distance between walls, height of door frames, position of lighting fixtures, and/or the like) and/or user data and/or characteristics (e.g., height, weight, BMI, user build data, user vital sign data, user skin characteristics, user diet and/or nutrition information, and/or the like).

At block S405, the first set of sensors sense raw sensor data for states of activities. The activities are typically human activities sensed by the sensors. Examples of activities are moving, breathing, stepping, talking, falling, opening or closing a door, opening or closing a window, climbing up or down stairs, opening or closing a refrigerator or cabinet, and so on. Examples of sensing including visualizing, hearing, smelling (e.g., detecting a chemical), and feeling (e.g., detecting a change in pressure), and the activity will be understood based on the type and placement of any sensor as well as what is sensed. The states of activities reflect differences in statuses of the sensors, such as, for example, changes from quiet to noisy, dark to light, off to on, or other binary changes in states of activities. Therefore, the states are a progression of states over time, such as State1 at Time1, State1 at Time2, State1 at Time3, State2 at Time4, and so on. Additionally, the states are not limited to binary possibilities, as sensors may be configured to detect more than two states such as ten or one hundred levels or a continuous observation (rather than discrete) of sound or light.

At block S406, a system may receive activity-specific streams of raw data captured by sensors and/or model activity-specific streams of raw data. The activity-specific streams of raw data are based on the progression of states of activity sensed by the sensor over time. For example, a sensor may sense dozens, hundreds, thousands or millions of states of activities over time and send the detected states as raw data continuously, in batches, or on-demand when requested.

At block S407A, time-series observations of the progression of states are identified using separate models for the raw data for each activity-specific stream from each of the first set of sensors. That is, each of the sensors placed at block S404 may source raw data, and a separate model may be applied for each activity sensed by each sensor. Thus, when a first sensor senses a progression of states for a first activity and a progression of states for a second activity, separate models may be applied for each of the first activity and the second activity sensed by the first sensor. When a second sensor senses a progression of states for the same first activity and a progression of states for the same second activity, additional separate models may be applied for each of the first activity and the second activity sensed by the second sensor. The models may be the same model with the same or different input settings, so that the time-series progressions of states for each activity-specific stream for (from) different sensors are comparable in that they are modeled by the same type of model even if different input settings are used for different activity-specific streams.

At block S407B, the time-series observations of progressions of states may be analyzed to determine a relative amount/volume/number of progressions from any one state to any other state for each activity-specific time-series. That is, given a number of progressions from state to state in any one time-series of observations, the analysis may be to see the number of times each stays the same or transits to each other possible state. The determination of the number of progressions from one state to any other state can be performed initially as a count, and then as a comparison that will show which transitions from a state are most likely and the likelihood of any one state transiting to any next state (i.e., the same state or any different state). As noted, the analysis at S407B may be performed for each time-series observation of states for each activity sensed by each sensor.

At block S408, a system may encode activity-specific time-series observations in separate models so as to generate encoded activity-specific time-series observations in the separate activity-specific models. For example, activity-specific time-series observations may be encoded in separate hidden Markov models (HMM), thereby directly embedding the temporal information of sensor data streams as a dynamic stochastic process. Hidden Markov model is a Bayesian network with discrete hidden states and output units that may represent both discrete and continuous observations. Continuous HMMs may encode sequential observations as a stochastic process whose dynamics is described by the hidden state variable varying between N hidden state values. The transition between hidden state values may be governed by transition probabilities represented by an N×N state transition matrix. The observable layer of HMM may consist of output units each associated with a hidden state value. HMMs may model multivariate observations of M channels. The distribution of outputs at each hidden state may be modeled using a mixture of Gaussian distributions. The mixture of Gaussian outputs may be well-suited for cases with multiple within-class modes of observations.

A left-to-right HMM configuration may be used to account for a lack of cyclic movements and other data points that often progress from a starting point to an ending point. Given N multivariate time-series observations ($x_1$ to $x_N$) each belonging to one of K classes, class-specific HMMs are trained for every channel m∈1, M; $\lambda_{MK}$: HMM model trained on $m^{th}$ channel for $k^{th}$ class.

At block S409, the probability for each state of each activity progressing next to each state for the same activity is determined. In this way, a transition between one state and the next is determined as a probability of progressing from one state to the next for each possible next state. The probability determined at S409 is determined for each activity sensed by each sensor.

At block S410, a system may project sensor data streams in posterior space of resulting activity-specific models. For example, for every observation O sensed by mth sensor, the probabilities that the observation is generated by the class-specific models ($\lambda_{mk}$, k=1, ... K) are computed (posterior probability: P (O|$\lambda_{mk}$) using the forward algorithm. The projection is a K-dimensional projection with each dimension corresponding to a probability distribution associated with a class, and the probability distributions for each activity sensed by each sensor can therefore be subject to comparisons given the projection onto K dimensions.

At block S412, a system may compute distances between activity-specific probability distributions. For example, pairwise symmetric Kullback-Leibler (KL) distances between the resulting posteriors based on divergence may be used as the shared probabilistic representation of the observations.

At block S414, a system may aggregate resulting probability distances to obtain shared probabilistic representations of sensor data.

At block S416, a system may weight dimensions of resulting shared probabilistic spaces according to their relevance to distinguish between different events and/or activities. For example, grouping channel-specific distances, group Lasso regression may then be performed in the resulting shared probabilistic space. Group Lasso, for example, may suppose there are G groups of features, each including $K_g$ members. A group Lasso optimization may be formulated as $$\min_{\beta_1,...,\beta_G} \left\| y - \sum_{g=1}^{G} \beta_g^T X_g \right\|^2, \text{ s.t.: } \sum_{g=1}^{G} \sqrt{\beta_g^T \beta_g} \leq s, \quad (1)$$

where Xg is the representation of independent variables over a collection of features in group g, $\beta_g$ carries the corresponding coefficients for the individual members of the group g, y is the response variable, and s is a constant defining the upper bound on the sparsity constraint. Introducing Lagrange multiplier γ, the resulting group Lasso minimization can be rewritten as.

$$\min_{\beta_1,...,\beta_G} \left\| y - \sum_{g=1}^{G} \beta_g^T X_g \right\|^2 + \gamma \sum_{g=1}^{G} \|\beta_g\|. \quad (2)$$

At block S418, a system may identify a minimal set of sensors most salient for tracking and detecting events and/or activities of interest. For example, selected groups of distances may correspond to channels most salient to discriminating between time-series observations.

At block S422, the method may end.

It is further noted that the systems and methods described herein may be tangibly embodied in one of more physical media, such as, but not limited to, a compact disc (CD), a digital versatile disc (DVD), a floppy disk, a hard drive, read only memory (ROM), random access memory (RAM), as well as other physical media capable of storing software, or combinations thereof. Moreover, the figures illustrate various components (e.g., servers, computers, processors, etc.) separately. The functions described as being performed at various components may be performed at other components, and the various components bay be combined or separated. Other modifications also may be made.

Figure 5:
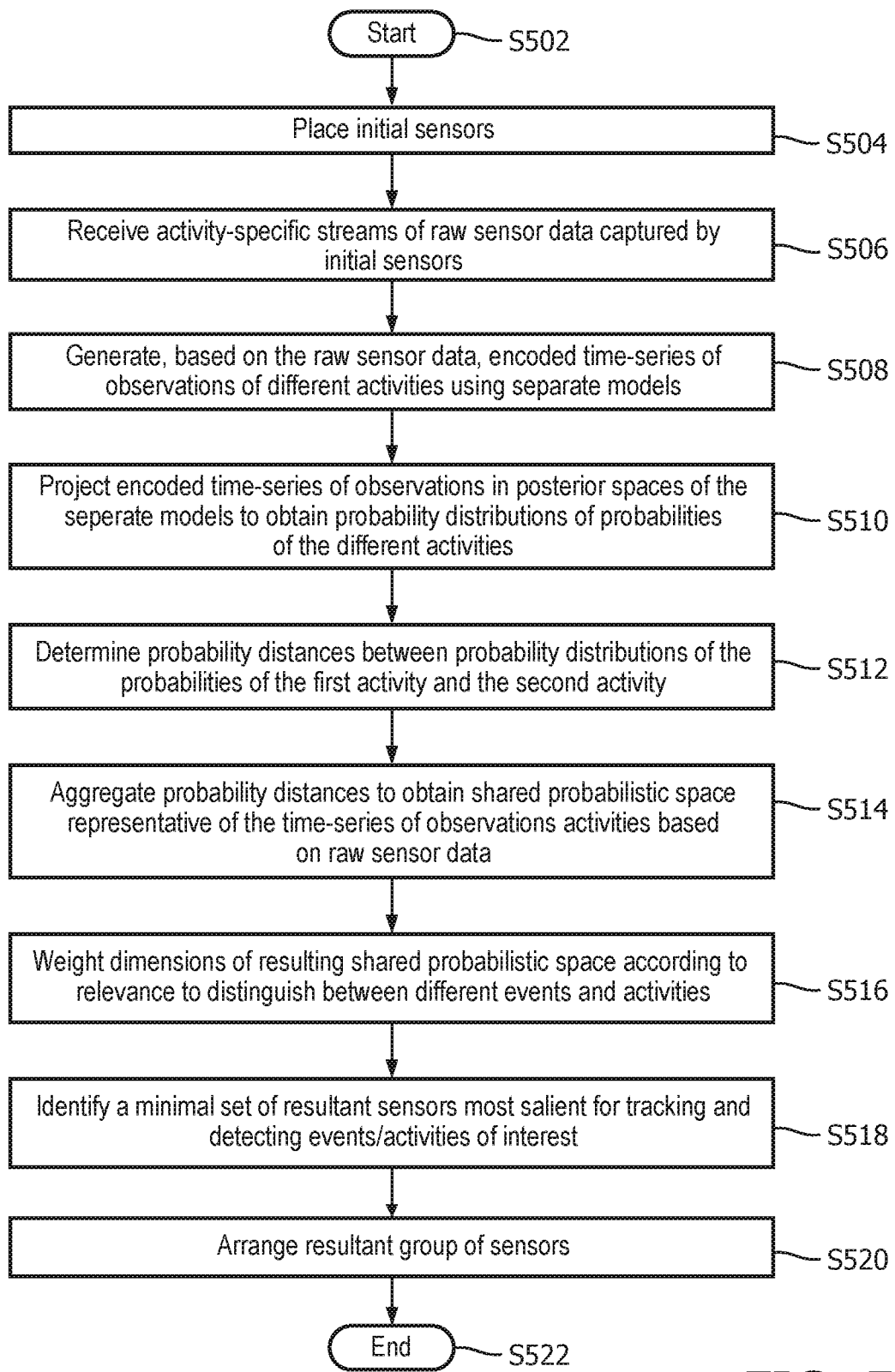
FIG. 5 illustrates another process for determining an arrangement of sensors, in accordance with a representative embodiment.

FIG. 5 illustrates another process for determining an arrangement of sensors, in accordance with a representative embodiment.

In the embodiment of FIG. 5, initial sensors are placed at S504.

At S506, activity-specific streams of raw sensor data captured by the initial sensors may be received.

At S508, encoded time-series of observations of different activities may be generated based on the raw sensor data using separate models.

At S510, the encoded time-series of observations may be projected in posterior spaces of the separate models to obtain the probability distributions of the different activities sensed by the different sensors.

At S512, the probability distances between probability distributions of the first activity and the second activity may be determined.

At S514, probability distances may be aggregated to obtain shared probabilistic space representative of the time-series of observations activities based on raw sensor data.

At S516, dimensions of the resulting shared probabilistic space may be weighted according to their relevance to distinguish between different events and activities.

At S518, a minimal resultant group of sensors most salient for tracking and detecting events/activities of interest may be identified. The minimal resultant group identified at S518 may be a subset of the initial sensors. At S520, the resultant sensors may be arranged. The arranging at S520 may be by a technician such as by removing one or more of the initial sensors, moving one or more of the initial sensors, and/or adding a new sensor to the initial sensors. The arranging at S520 will typically result in fewer sensors than the initial sensors. Additionally, the arranging at S520 may be performed by simply remotely deactivating one or more of the initial sensors that are already in place. As a result, the sensor required for an arrangement is reduced, and the sensor streams being monitored is reduced to those salient for tracking a user's activities of interest. Thus, the minimal resultant group is optimized in terms of location (e.g., locations in a home) as well as in number based on the process of FIG. 5 as well as for other embodiments described herein.

Figure 6:
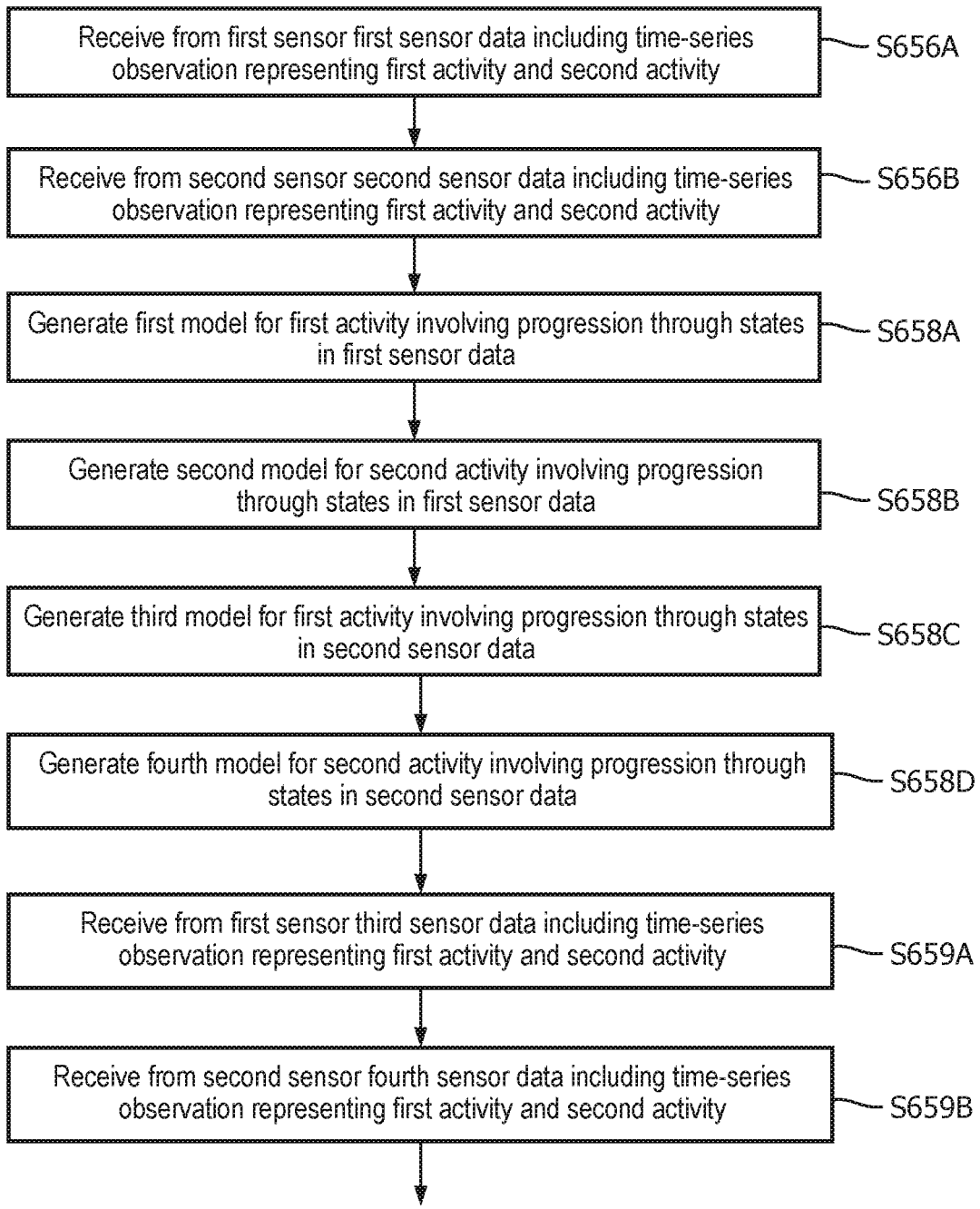
FIG. 6 illustrates another process for determining an arrangement of sensors, in accordance with a representative embodiment.
Figure 6:
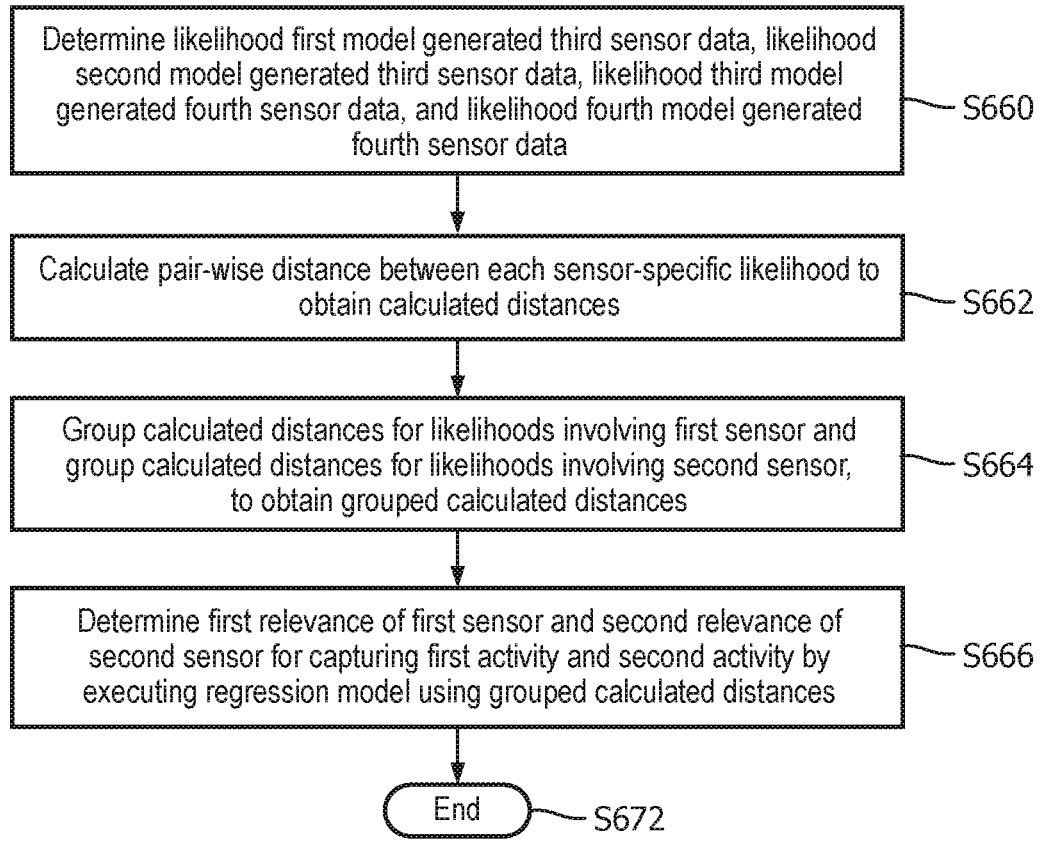

FIG. 6 illustrates another process for determining an arrangement of sensors, in accordance with a representative embodiment.

In FIG. 6, the process starts at S656A by receiving, from a first sensor, first sensor data including time-series observation representing a first activity and a second activity. At S656B, second sensor data may be received from a second sensor. The second sensor data includes time-series observation representing the first activity and the second activity. The operations at S656A and S656B may be similar or identical to the operations at S506 in FIG. 5.

At S658A, a first model for first activity is generated. The first activity, as is the case with most or all activity described herein, involves a progression through states sensed by a sensor, in this case by the first sensor. At S658B, a second model for second activity is generated. The second activity may also involves a progression through states sensed by a sensor, in this case also the first sensor. At S658C, a third model for the first activity may be generated. The first activity now involves a progression through states sensed by the second sensor. At S658D, a fourth model for the second activity may be generated. The second activity also now involves a progression through states sensed by the second sensor.

At S659A, third sensor data is received from the first sensor. The third sensor data includes time-series observation again representing the first activity and the second activity. At S659B, fourth sensor data is received from the second sensor. The fourth sensor data also includes time-series observation again representing the first activity and the second activity.

At S660, the likelihood that the first model generated the third sensor data is determined. The likelihood that the second model generated the third sensor data may also be determined. The likelihood that the third model generated the fourth sensor data may be determined. The likelihood that the fourth model generated the fourth sensor data may also be determined. Here, the first model, the second model, the third model, and the fourth model may be used to ultimately determine their effectiveness (e.g., relevancy) in capturing first activity and second activity after the models are generated.

At S662, pair-wise distance between each sensor-specific likelihood may be calculated to obtain calculated distances.

At S664, calculated distances for likelihoods involving the first sensor may be grouped, and calculated distances for likelihoods involving the second sensor may be grouped. As a result of the grouping at S664, grouped calculated distances may be obtained.

At S666, the process may determine a first relevance of the first sensor and a second relevance of the second sensor for capturing first activity and second activity. The first relevance and the second relevance may be determined by executing a regression model using the grouped calculated distances in order to determine the effectiveness of each sensor in capturing the activities of interest.

In FIG. 6, the process can be used to identify an arrangement of sensors for monitoring a space. The arrangement can be identified by and defined by characteristics of the space, which in turn may be input to the modeling in FIG. 6 as a priori settings, and which can also be reflected by the data streams of raw data output from the sensors. The space may be enclosed, such as a living space for a user, such as house or apartment with different rooms primarily used for different purposes.

As an example, a sensor may not be as relevant to an activity if the sensor is too far away from the activity, if a physical obstruction is between the sensor and the activity, if the sensor is pointed in a direction away from the activity, or if the sensor simply does not sense a characteristic of the activity that can be sensed (e.g., a noise sensor may not sense a quiet movement).

The process of FIG. 6 may coincide with or include features of the process of FIG. 4 and the process of FIG. 5. For example, identifying a minimized subset of sensors from the initial set of sensors as in S418 and S518 may be performed to coincide with or result from determining the relevance of sensors as in S666. Additionally, arranging the resultant group of sensors (i.e., the minimized subset) as in S520 may be performed as a result of determining the relevance of sensors as in S666.

Additionally, the relevance of the sensors determined at S666 is reflective of their utility in observing activities of interest. Thus, the likelihoods of the different models generating the newer sensor data is useful in determining the relevance of the sensors that generate the newer sensor data. As a result, whether a sensor is included or excluded in the determined arrangement following the process of FIG. 6 is tied to the likelihood of the models corresponding to the sensor actually generating the newer sensor data after the models are generated.

Figure 7:
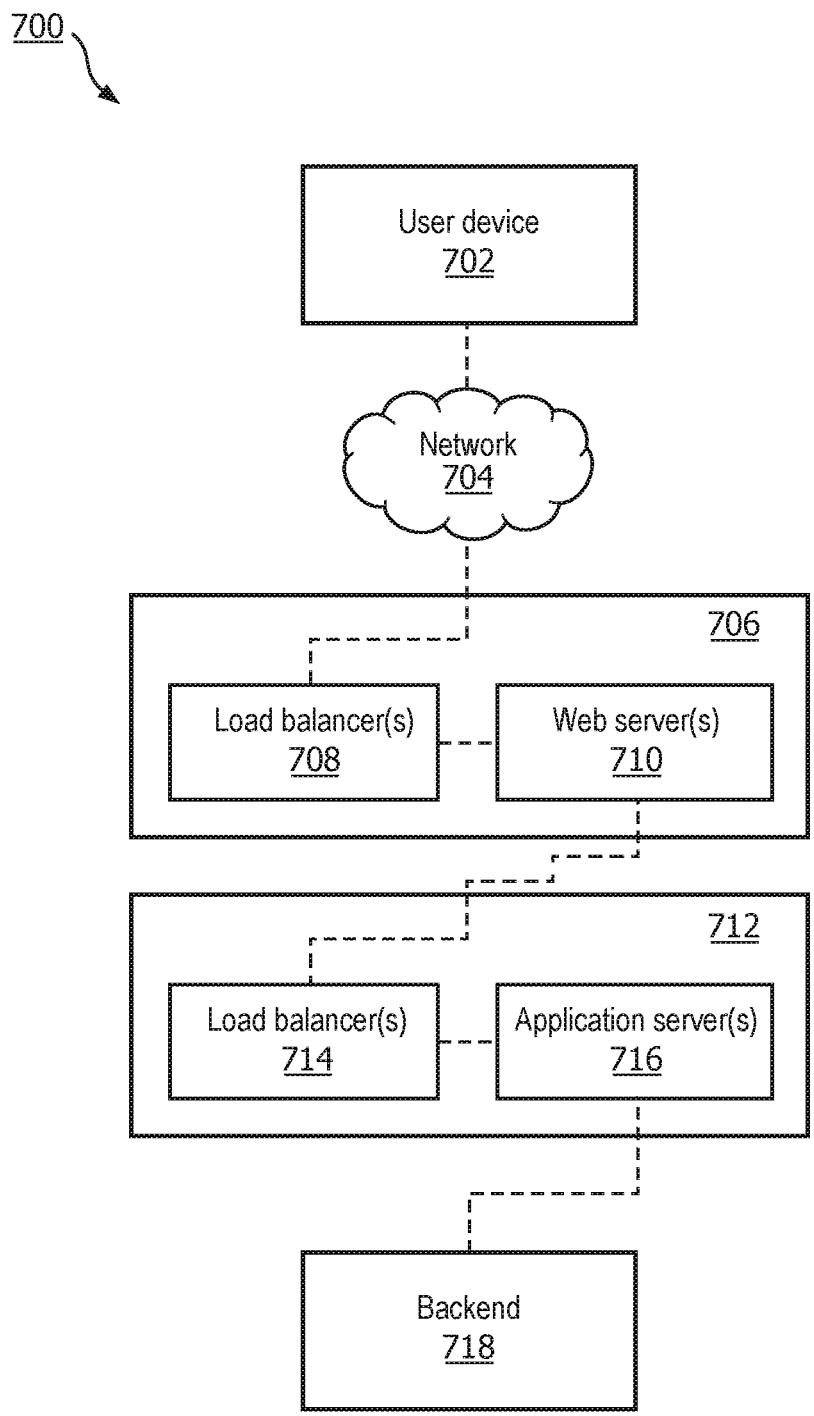
FIG. 7 is an illustrative view of another system for determining an arrangement of sensors, in accordance with a representative embodiment.

FIG. 7 is an illustrative view of another system for determining an arrangement of sensors, in accordance with a representative embodiment.

FIG. 7 depicts a system 700 used in determining an optimal sensor configuration for ambient and/or physiological sensing technologies. The system 700 in FIG. 7 may enable a backend system, such as the system 300 for example, to provide network services to users associated with user devices, such as mobile and/or client devices that may communicate with a backend system. As shown in FIG. 7, the system 700 may include a user device 702, a network 704, a front-end controlled domain 706, a back-end controlled domain 712, and a backend 718. Front-end controlled domain 706 may include one or more load balancer(s) 708 and one or more web server(s) 710. Back-end controlled domain 712 may include one or more load balancer(s) 714 and one or more application server(s) 716.

The user device 702 may be a network-enabled computer such as a client device. As referred to herein, a network-enabled computer may include, but is not limited to: e.g., any computer device, or communications device including, e.g., a server, a network appliance, a personal computer (PC), a workstation, a mobile device, a phone, a handheld PC, a personal digital assistant (PDA), a thin client, a fat client, an Internet browser, or other device. The one or more network-enabled computers of the system 700 may execute one or more software applications to enable, for example, network communications.

User device 702 also may be a mobile device. For example, a mobile device may include an iPhone, iPod, iPad from Apple® or any other mobile device running Apple's iOS operating system, any device running Google's Android® operating system, including for example, Google's wearable device, Google Glass, any device running Microsoft's Windows® Mobile operating system, and/or any other smartphone or like wearable mobile device.

Network 704 may be one or more of a wireless network, a wired network, or any combination of a wireless network and a wired network. For example, network 704 may include one or more of a fiber optics network, a passive optical network, a cable network, an Internet network, a satellite network, a wireless LAN, a Global System for Mobile Communication (GSM), a Personal Communication Service (PCS), a Personal Area Networks, (PAN), D-AMPS, Wi-Fi, Fixed Wireless Data, IEEE 802.11b, 802.15.1, 802.11n, and 802.11g or any other wired or wireless network for transmitting and receiving a data signal.

In addition, network 704 may include, without limitation, telephone lines, fiber optics, IEEE Ethernet 902.3, a wide area network (WAN), a local area network (LAN) or a global network such as the Internet. Also, network 704 may support an Internet network, a wireless communication network, a cellular network, or the like, or any combination thereof. Network 704 may further include one network, or any number of example types of networks mentioned above, operating as a stand-alone network or in cooperation with each other. Network 704 may utilize one or more protocols of one or more network elements to which they are communicatively couples. Network 704 may translate to or from other protocols to one or more protocols of network devices. Although network 704 is depicted as a single network, it should be appreciated that according to one or more embodiments, network 704 may include multiple interconnected networks, such as, for example, the Internet, a service provider's network, a cable television network, corporate networks, and home networks.

Front-end controlled domain 706 may be implemented to provide security for backend 718. Load balancer(s) 708 may distribute workloads across multiple computing resources, such as, for example computers, a computer cluster, network links, central processing units or disk drives. In various embodiments, load balancer(s) 708 may distribute workloads across, for example, web server(s) 710. Load balancing aims to optimize resource use, maximize throughput, minimize response time, and avoid overload of any one of the resources. Using multiple components with load balancing instead of a single component may increase reliability through redundancy. Load balancing is usually provided by dedicated software or hardware, such as a multilayer switch or a Domain Name System (DNS) server process.

Load balancer(s) 708 may include software that monitoring the port where external clients, such as, for example, user device 702, connect to access various services of a backend system, for example. Load balancer(s) 708 may forward requests to one of the application server(s) 716 and/or backend 718 servers, which may then reply to load balancer(s) 708. This may allow load balancer(s) 708 to reply to user device 702 without user device 702 ever knowing about the internal separation of functions. It also may prevent user devices from contacting backend servers directly, which may have security benefits by hiding the structure of the internal network and preventing attacks on backend 718 or unrelated services running on other ports, for example.

A variety of scheduling algorithms may be used by load balancer(s) 708 to determine which backend server to send a request to. Simple algorithms may include, for example, random choice or round robin. Load balancer(s) 708 also may account for additional factors, such as a server's reported load, recent response times, up/down status (determined by a monitoring poll of some kind), number of active connections, geographic location, capabilities, or how much traffic it has recently been assigned.

Load balancer(s) 708 may be implemented in hardware and/or software. Load balancer(s) 708 may implement numerous features, including, without limitation: asymmetric loading; Priority activation: SSL Offload and Acceleration; Distributed Denial of Service (DDoS) attack protection; HTTP/HTTPS compression; TCP offloading; TCP buffering; direct server return; health checking; HTTP/HTTPS caching; content filtering; HTTP/HTTPS security; priority queuing; rate shaping; content-aware switching; client authentication; programmatic traffic manipulation; firewall; intrusion prevention systems.

Web server(s) 710 may include hardware (e.g., one or more computers) and/or software (e.g., one or more applications) that deliver web content that can be accessed by, for example a client device (e.g., user device 702) through a network (e.g., network 704), such as the Internet. In various examples, web servers, may deliver web pages, relating to, for example, sensor configuration optimization and the like, to clients (e.g., user device 702). Web server(s) 710 may use, for example, a hypertext transfer protocol (HTTP/HTTPS or sHTTP) to communicate with user device 702. The web pages delivered to client device may include, for example, HTML documents, which may include images, style sheets and scripts in addition to text content.

A user agent, such as, for example, a web browser, web crawler, or native mobile application, may initiate communication by making a request for a specific resource using HTTP/HTTPS and web server(s) 710 may respond with the content of that resource or an error message if unable to do so. The resource may be, for example a file stored on backend 718. Web server(s) 710 also may enable or facilitate receiving content from user device 702 so user device 702 may be able to, for example, submit web forms, including uploading of files.

Web server(s) also may support server-side scripting using, for example, Active Server Pages (ASP), PHP, or other scripting languages. Accordingly, the behavior of web server(s) 710 can be scripted in separate files, while the actual server software remains unchanged.

Load balancer(s) 714 may be similar to load balancer(s) 708 as described above and may distribute workloads across application server(s) 716 and backend 718 server(s).

Application server(s) 716 may include hardware and/or software that is dedicated to the efficient execution of procedures (e.g., programs, routines, scripts) for supporting its applied applications. Application server(s) 716 may include one or more application server frameworks, including, for example, Java application servers (e.g., Java platform, Enterprise Edition (Java EE), the .NET framework from Microsoft®, PHP application servers, and the like). The various application server frameworks may contain a comprehensive service layer model. Also, application server(s) 716 may act as a set of components accessible to, for example, the system 700 that implements entities, through an API defined by the platform itself. For Web applications, these components may be performed in, for example, the same running environment as web server(s) 710, and application server(s) 716 may support the construction of dynamic pages. Application server(s) 716 also may implement services, such as, for example, clustering, failover, and load-balancing. In various embodiments, where application server(s) 716 are Java application servers, the application server(s) 716 may behave like an extended virtual machine for running applications, transparently handling connections to databases associated with backend 718 on one side, and, connections to the Web client (e.g., the user device 702) on the other.

Backend 718 may include hardware and/or software that enables the backend services of, for example, an entity that maintains a distributed system similar to the system 700. For example, backend 718 may include, a system capable of performing the methods disclosed herein, such as method 400 for example. Backend 718 may be associated with various databases. Backend 718 also may be associated with one or more servers that enable the various services provided by the system 700.

As described above, optimal sensor placement may be determined for ambient sensing technologies, physiological sensing technologies, and/or any combination thereof. The optimization of sensor placement and arrangement can be used to augment any multi-sensor, multi-modal distributed tracking technologies, including those relating to ambient monitoring of daily activities, as well as physiology (e.g., body area networks and patient monitoring).

For instance, in an ambient health monitoring setup, it is often unclear what type of sensor, how many of them and where in the room, should be deployed to enable seamless observation of user's ADLs and IADLs. Therefore, it is desired to identify the modalities and sensors salient to activities and events of interest (e.g. number and placement of motion sensors for tracking sleep in a bedroom). Even with a predefined number of sensors, a proper deployment of the sensors is critical for the optimal monitoring performance of an ambient sensing system.

As described above, relevance of sensors (e.g., a first sensor and a second sensor) to activities (e.g., a first activity and a second activity) can be identified by executing a regression model using grouped calculated probabilistic distances. The relevance can be identified even when representation of the observations is variable-length as is expected for sensor data collected in a naturalistic setting. Differences in sequence order of data primitives (states sensed by sensors), timing, phase, and other characteristics reflective of actual behavior can be accounted for in the optimization described herein. The optimal sensor deployment described herein also promotes less intrusive ambient sensing technologies by helping to reduce the number of required sensors to only those most salient for detecting the activity of interest. Therefore, the systematic approach described herein can help promote efficient, inexpensive, and accurate health-enabling and home-monitoring solutions.

Optimal sensor placement is also applicable to many other types of contexts in which multiple sensors are used, and optimization of the sensors may provide benefits. For example, in a utility system such as an electric network or water distribution system, different types of sensors may be placed in many different locations to monitor characteristics of the utility system. The number of sensors can be minimized by using the processing described herein to identify which sensors and which locations are salient to the activities being monitored, and thus the information being sought.

In another example, a complex industrial system may include different types of sensors placed in different locations to monitor different characteristics of the industrial system. The number and type of sensors being used may be optimized by starting with an excess of sensors placed in varying locations, and then performing the processing described herein to identify the minimal set of sensors salient to detect the activities being monitored and/or desired to be monitored. For example, mechanical motions of a component of an industrial system being monitored may be identified by a minimized set of one or more sensors selected according to the processing described herein.

Moreover, the cost of particular types of sensors can be taken into account in the processing, in that the saliency of sensors to monitoring different activities may vary based on the cost of the sensors. Accordingly, post-processing after the group LASSO optimization described herein can be used to adjust the results of regression analysis based on the relative cost of identified sensors relative to other sensors determined to otherwise be less than optimal.

As described above, the present disclosure is not to be limited in terms of the particular embodiments described in this application, which are intended as illustrations of various aspects. Many modifications and variations can be made without departing from its spirit and scope, as may be apparent. Functionally equivalent methods and apparatuses within the scope of the disclosure, in addition to those enumerated herein, may be apparent from the foregoing representative descriptions. Such modifications and variations are intended to fall within the scope of the appended representative claims. The present disclosure is to be limited only by the terms of the appended representative claims, along with the full scope of equivalents to which such representative claims are entitled. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It may be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It may be further understood by those within the art that if a specific number of an introduced claim recitation is intended, such an intent may be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It may be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" may be understood to include the possibilities of "A" or "B" or "A and B."

The foregoing description, along with its associated embodiments, has been presented for purposes of illustration only. It is not exhaustive and does not limit the concepts disclosed herein to their precise form disclosed. Those skilled in the art may appreciate from the foregoing description that modifications and variations are possible in light of the above teachings or may be acquired from practicing the disclosed embodiments. For example, the steps described need not be performed in the same sequence discussed or with the same degree of separation. Likewise various steps may be omitted, repeated, or combined, as necessary, to achieve the same or similar objectives. Accordingly, the present disclosure is not limited to the above-described embodiments, but instead is defined by the appended claims in light of their full scope of equivalents.

In the preceding specification, various preferred embodiments have been described with references to the accompanying drawings. It may, however, be evident that various modifications and changes may be made thereto, and additional embodiments may be implemented, without departing from the broader scope of the inventive concepts disclosed herein as set forth in the claims that follow. The specification and drawings are accordingly to be regarded as an illustrative rather than restrictive sense.

Although system and method of optimal sensor placement has been described with reference to several exemplary embodiments, it is understood that the words that have been used are words of description and illustration, rather than words of limitation. Changes may be made within the purview of the appended claims, as presently stated and as amended, without departing from the scope and spirit of system and method of optimal sensor placement in its aspects. Although system and method of optimal sensor placement has been described with reference to particular means, materials and embodiments, system and method of optimal sensor placement is not intended to be limited to the particulars disclosed; rather system and method of optimal sensor placement extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A controller for determining an arrangement of sensors for monitoring a space, comprising:
   a memory that stores instructions; and
   a processor that executes the instructions,
   wherein, when executed by the processor, the instructions cause the controller to execute a process comprising:
   receiving, from a first sensor of at least two sensors, a first sensor data comprising at least one time-series observation representing at least a first activity and a second activity;
   receiving, from a second sensor of the at least two sensors, a second sensor data comprising at least one time-series observation representing the first activity and the second activity;
   generating, by the processor, a first model for the first activity involving a first progression through a plurality of states indicated by at least a portion of the first sensor data;

generating, by the processor, a second model for the second activity involving a second progression through a plurality of states indicated by at least a portion of the first sensor data;

generating, by the processor, a third model for the first activity involving a third progression through a plurality of states indicated by at least a portion of the second sensor data;

generating, by the processor, a fourth model for the second activity involving a fourth progression through a plurality of states indicated by at least a portion of the second sensor data;

receiving, from the first sensor, a third sensor data comprising at least one time-series observation representing at least the first activity and the second activity;

receiving, from the second sensor, a fourth sensor data comprising at least one time-series observation representing at least the first activity and the second activity;

determining, using the processor, a likelihood that the first model generated at least a portion of the third sensor data, a likelihood that the second model generated at least a portion of the third sensor data, a likelihood that the third model generated at least a portion of the fourth sensor data, and a likelihood that the fourth model generated at least a portion of the fourth sensor data;

calculating, using the processor, a pair-wise distance between each sensor-specific determined likelihood to obtain calculated distances;

grouping, using the processor, the calculated distances for the likelihoods involving the first sensor, and grouping, using the processor, the calculated distances for the likelihoods involving the second sensor, to obtain grouped calculated distances, and determining, using the processor, a first relevance of the first sensor and a second relevance of the second sensor for capturing the first activity and the second activity by executing a regression model using the grouped calculated distances, wherein one of the first sensor and the second sensor is included in an arrangement of sensors used to monitor the space based on the first relevance and the second relevance determined using the processor and the other of the first sensor and the second sensor is excluded in the arrangement of sensors used to monitor the space based on the first relevance and the second relevance determined using the processor.

2. The controller of claim 1, wherein the process executed by the controller further comprises:
performing one of: activating the first sensor based on the first relevance or removing the first sensor based on the first relevance.

3. The controller of claim 1, wherein the process executed by the controller further comprises:
performing one of: activating the second sensor based on the second relevance or removing the second sensor based on the second relevance.

4. The controller of claim 1, wherein the process executed by the controller further comprises:
receiving, from a third sensor of the at least two sensors, a fifth sensor data comprising at least one time-series observation representing the first activity and the second activity;

generating, by the processor, a fifth model for the first activity involving a fifth progression through a plurality of states indicated by at least a portion of the fifth sensor data;

generating, by the processor, a sixth model for the second activity involving a sixth progression through a plurality of states indicated by at least a portion of the fifth sensor data;

receiving, from the third sensor, a sixth sensor data comprising at least one time-series observation representing at least the first activity and the second activity; and determining, using the processor, a likelihood that the fifth model generated at least a portion of the sixth sensor data, and a likelihood that the sixth model generated at least a portion of the sixth sensor data.

5. The controller of claim 1, wherein the first sensor comprises a first group of sensors, and wherein the second sensor comprises a second group of sensors.

6. The controller of claim 1, wherein the first sensor data comprises a first time-series observation representing a first activity and a second time-series observation representing a second activity.

7. The controller of claim 1, wherein the first model comprises a probabilistic graphical model.

8. The controller of claim 1, wherein the sensor-specific determined likelihood represents determined likelihoods associated with the first sensor and determined likelihoods associated with the second sensor.

9. The controller of claim 1, wherein the regression model is a multinomial logistic regression model with a group LASSO penalty.

10. The controller of claim 9, wherein the multinomial logistic regression model is a binomial logistic regression model with a group LASSO penalty.

11. The controller of claim 1, wherein the regression model determines weights of the grouped calculated distances such that they best represent the first activity and the second activity.

12. The controller of claim 1, wherein the process executed by the controller further comprises:
identifying, from the at least two sensors, a minimal set of sensors most salient for sensing the first activity and the second activity.

13. The controller of claim 12,
wherein the minimal set of sensors is selected as a subset of the at least two sensors.

14. The controller of claim 1, wherein the first model, the second model, the third model and the fourth model each comprise a separate hidden Markov model.

15. The controller of claim 1, wherein the arrangement is defined by characteristics of the space being monitored.

16. A method for determining an arrangement of sensors for monitoring a space, comprising:
receiving, from a first sensor of at least two sensors, a first sensor data comprising at least one time-series observation representing at least a first activity and a second activity;

receiving, from a second sensor of the at least two sensors, a second sensor data comprising at least one time-series observation representing the first activity and the second activity;

generating, by a processor, a first model for the first activity involving a first progression through a plurality of states indicated by at least a portion of the first sensor data;

generating, by the processor, a second model for the second activity involving a second progression through a plurality of states indicated by at least a portion of the first sensor data;

generating, by the processor, a third model for the first activity involving a third progression through a plurality of states indicated by at least a portion of the second sensor data;

generating, by the processor, a fourth model for the second activity involving a fourth progression through a plurality of states indicated by at least a portion of the second sensor data;

receiving, from the first sensor, a third sensor data comprising at least one time-series observation representing at least the first activity and the second activity;

receiving, from the second sensor, a fourth sensor data comprising at least one time-series observation representing at least the first activity and the second activity;

determining, using the processor, a likelihood that the first model generated at least a portion of the third sensor data, a likelihood that the second model generated at least a portion of the third sensor data, a likelihood that the third model generated at least a portion of the fourth sensor data, and a likelihood that the fourth model generated at least a portion of the fourth sensor data;

calculating, using the processor, a pair-wise distance between each sensor-specific determined likelihood to obtain calculated distances;

grouping, using the processor, the calculated distances for the likelihoods involving the first sensor, and grouping, using the processor, the calculated distances for the likelihoods involving the second sensor, to obtain grouped calculated distances; and determining, using the processor, a first relevance of the first sensor and a second relevance of the second sensor for capturing the first activity and the second activity by executing a regression model using the grouped calculated distances, wherein one of the first sensor and the second sensor is included in an arrangement of sensors used to monitor the space based on the first relevance and the second relevance determined using the processor, and the other of the first sensor and the second sensor is excluded in the arrangement of sensors used to monitor the space based on the first relevance and the second relevance determined using the processor.

17. The method of claim 16, further comprising:

arranging a minimized group of sensors to monitor the space based on the at least two sensors, wherein the minimized group excludes at least one of the at least two sensors.

18. A system for determining an arrangement of sensors for monitoring a space, comprising:

a communication interface used to communicate over a communications network;

a user interface; and a controller comprising a memory that stores instructions, and a processor that executes the instructions, wherein, when executed by the processor, the instructions cause the system to execute a process comprising:

receiving, from a first sensor of at least two sensors, a first sensor data comprising at least one time-series observation representing at least a first activity and a second activity;

receiving, from a second sensor of the at least two sensors, a second sensor data comprising at least one time-series observation representing the first activity and the second activity;

generating, by the processor, a first model for the first activity involving a first progression through a plurality of states indicated by at least a portion of the first sensor data;

generating, by the processor, a second model for the second activity involving a second progression through a plurality of states indicated by at least a portion of the first sensor data;

generating, by the processor, a third model for the first activity involving a third progression through a plurality of states indicated by at least a portion of the second sensor data;

generating, by the processor, a fourth model for the second activity involving a fourth progression through a plurality of states indicated by at least a portion of the second sensor data;

receiving, from the first sensor, a third sensor data comprising at least one time-series observation representing at least the first activity and the second activity;

receiving, from the second sensor, a fourth sensor data comprising at least one time-series observation representing at least the first activity and the second activity;

determining, using the processor, a likelihood that the first model generated at least a portion of the third sensor data, a likelihood that the second model generated at least a portion of the third sensor data, a likelihood that the third model generated at least a portion of the fourth sensor data, and a likelihood that the fourth model generated at least a portion of the fourth sensor data;

calculating, using the processor, a pair-wise distance between each sensor-specific determined likelihood to obtain calculated distances;

grouping, using the processor, the calculated distances for the likelihoods involving the first sensor, and grouping, using the processor, the calculated distances for the likelihoods involving the second sensor, to obtain grouped calculated distances; and determining, using the processor, a first relevance of the first sensor and a second relevance of the second sensor for capturing the first activity and the second activity by executing a regression model using the grouped calculated distances, wherein one of the first sensor and the second sensor is included in an arrangement of sensors used to monitor the space based on the first relevance and the second relevance determined using the processor, and the other of the first sensor and the second sensor is excluded in the arrangement of sensors used to monitor the space based on the first relevance and the second relevance determined using the processor.

19. The system of claim 18, wherein the space comprises an enclosed living space.

* * * * *